(12) United States Patent
Gerster et al.

(10) Patent No.: US 7,148,232 B2
(45) Date of Patent: Dec. 12, 2006

(54) OXAZOLO, THIAZOLO AND SELENAZOLO [4,5-C]-QUINOLIN-4-AMINES AND ANALOGS THEREOF

(75) Inventors: John F. Gerster, Woodbury, MN (US); Kyle J. Lindstrom, Houlton, WI (US); Gregory J. Marszalek, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 62 days.

(21) Appl. No.: 10/926,385

(22) Filed: Aug. 25, 2004

(65) Prior Publication Data
US 2005/0026943 A1    Feb. 3, 2005

Related U.S. Application Data

(62) Division of application No. 10/726,131, filed on Dec. 2, 2003, now Pat. No. 6,809,203, which is a division of application No. 10/370,804, filed on Feb. 20, 2003, now Pat. No. 6,703,402, which is a division of application No. 10/192,416, filed on Jul. 10, 2002, now Pat. No. 6,627,640, which is a division of application No. 09/961,738, filed on Sep. 24, 2001, now Pat. No. 6,440,992, which is a division of application No. 09/593,434, filed on Jun. 14, 2000, now Pat. No. 6,323,200, which is a division of application No. 09/361,544, filed on Jul. 27, 1999, now Pat. No. 6,110,929.

(60) Provisional application No. 60/094,346, filed on Jul. 28, 1998.

(51) Int. Cl.
*A61K 31/4355* (2006.01)
*A61K 31/4365* (2006.01)
*C07D 42/14* (2006.01)
*C07D 42/04* (2006.01)

(52) U.S. Cl. .................. 514/293; 514/291; 546/81; 546/82; 546/80; 546/83

(58) Field of Classification Search ................. 546/81, 546/82, 80, 83; 514/293, 291
See application file for complete search history.

(56) References Cited

U.S. PATENT DOCUMENTS

| | | | |
|---|---|---|---|
| 4,031,230 A | 6/1977 | Gottschlich et al. |
| 4,038,396 A | 7/1977 | Shen et al. |
| 4,131,677 A | 12/1978 | Shen et al. |
| 4,689,338 A | 8/1987 | Gerster et al. |
| 4,698,348 A | 10/1987 | Gerster |
| 4,778,811 A | 10/1988 | Knoll et al. |
| 4,904,669 A | 2/1990 | Knoll et al. |
| 4,929,624 A | 5/1990 | Gerster et al. |
| 5,037,986 A | 8/1991 | Gerster |
| 5,268,376 A | 12/1993 | Gester |
| 5,312,822 A | 5/1994 | Albaugh |
| 5,346,905 A | 9/1994 | Gerster |
| 5,352,784 A | 10/1994 | Nikolaides et al. |
| 5,389,640 A | 2/1995 | Gerster et al. |
| 5,446,153 A | 8/1995 | Lindstrom et al. |
| 5,451,585 A | 9/1995 | Albaugh |
| 5,482,936 A | 1/1996 | Lindstrom |
| 5,605,899 A | 2/1997 | Gerster et al. |

FOREIGN PATENT DOCUMENTS

| | | |
|---|---|---|
| EP | 0 055 248 | 6/1982 |
| GB | 2 184 117 | 6/1987 |
| WO | WO 93/05042 | 3/1993 |
| WO | WO 95/02597 | 1/1995 |
| WO | WO 95/02598 | 1/1995 |
| WO | WO 98/16514 | 4/1998 |
| WO | WO 98/42712 | 10/1998 |

OTHER PUBLICATIONS

Tetrahedron Letters, vol. 22, No. 22, pp. 2121-2124, 1981 Printed in Great Britain.
Chem. Abstract 95:114500, (1981).
Chem. Abstract 86:16608, (1977).
Temple, Smith Kussner, and Montgomery, "Synthesis of Imidazo [4,5-b]pyridines and V-Triazolo [4,5-b]pyridines. Preparation of 1-Deaza-6-thioguanine Analogues", J. Org. Chem, vol. 41, No. 24, 1976, pp. 3784-3788.
Bachman et al., *J. Org. Chem.* 15, 1278-1284 (1950).
Jain et al., *J. Med. Chem.* 11, pp. 87-92 (1968).
Baranov et al., *Chem. Abs.* 85, 94362 (1976).
Berenyi et al., *J. Heterocyclic Chem.* 18, 1537-1540 (1981).
Berge SM, et al., "Pharmaceutical Salts," *J. Pharm. Sci.* 1977;66:1.
Bachman et. al., *Journal of the American Chemical Society*, 69, pp. 365-371 (1947).
Ambrogi et. al., *Synthesis*, pp. 656-658 (1992).
Adler et. al., *Journal of the Chemical Society*, pp. 1794-1797 (1960).
Süs et. al., *Justus Liebigs Annalen der Chemie*, 583, pp. 150-160 (1953).
Süs et. al., *Justus Liebigs Annalen der Chemie*, 593, pp. 91-126 (1955).
G. L. Brennan and L. H. Kronenberg in "Automated Bioassay of Interferons in Micro-test Plates", Biotechniques, Jun./Jul. 78, 1983.
Testerman et. al. In "Cytokine Induction by the Immunomodulators Imiquimod and S-27609", *Journal of Leukocyte Biology*, 58, 365-372 (Sep. 1995).
Korolkovas, "Essentials of Medicinal Chemistry", 2nd Edition, John Wiley & Sons, NY, p. 78, paragraph "f"and p. 80, Table 2.9 (1988).

*Primary Examiner*—Rita Desai
(74) *Attorney, Agent, or Firm*—Dean Ersfeld

(57) ABSTRACT

Thiazolo-, oxazolo- and selenazolo[4,5-c]quinolin-4-amines and analogs thereof are described including methods of manufacture and the use of novel intermediates. The compounds are immunomodulators and induce cytokine biosynthesis, including interferon and/or tumor biosynthesis, necrosis factor, and inhibit the T-helper-type 2 immune response. The compounds are further useful in the treatment of viral and neoplastic diseases.

3 Claims, No Drawings

OXAZOLO, THIAZOLO AND SELENAZOLO [4,5-C]-QUINOLIN-4-AMINES AND ANALOGS THEREOF

CROSS REFERENCE TO RELATED APPLICATIONS

This application is a divisional of U.S. application Ser. No. 10/726,131, filed Dec. 2, 2003, now U.S. Pat. No. 6,809,203, which is a divisional of U.S. application Ser. No. 10/370,804, filed Feb. 20, 2003, now U.S. Pat. No. 6,703, 402, which is a divisional of U.S. application Ser. No. 10/192,416, filed July 10, 2002, now U.S. Pat. No. 6,627, 640, which is a divisional of U.S. application Ser. No. 09/961,738, filed on Sep. 24, 2001, issued as U.S. Pat. No. 6,440,992, which is a divisional of U.S. application Ser. No. 09/593,434, filed Jun. 14, 2000, issued as U.S. Pat. No. 6,323,200, which is a divisional of U.S. application Ser. No. 09/361,544, filed Jul. 27, 1999, issued as U.S. Pat. No. 6,110,929, which claims benefit of Provisional Application No. 60/094,346 filed Jul. 28, 1998.

FIELD OF THE INVENTION

This invention relates to oxazolo, thiazolo and selenazolo [4,5-c]-quinolin-, tetrahydroquinolin-4-amines and hetero analogs thereof, and to intermediates used in their preparation. The invention also relates to pharmaceutical compositions containing the above compounds as well as the use of these compounds as immunomodulators and for inducing cytokine biosynthesis, including interferon-α biosynthesis and/or tumor necrosis factor-α biosynthesis.

BACKGROUND OF THE INVENTION AND RELATED PRIOR ART

The first reliable report on the 1H-imidazo[4,5-c]quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines have been reported. For example, Jain et al., *J. Med. Chem.* 11, pp. 87–92 (1968), has synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), and Berenyi et al., *J. Heterocyclic Chem.* 18, 1537–1540 (1981), have reported certain 2-oxoimidazo[4,5-c]quinolines.

Following the above report, 1H-imidazo[4,5-c]quinolin-4-amines and 1- and 2-substituted derivatives thereof were found to be useful as antiviral agents, bronchodilators and immunomodulators. These are described in U.S. Pat. Nos. 4,689,338; 4,698,348; 4,929,624; 5,037,986; 5,266,675; 5,268,376; 5,346,905; 5,389,640; 5,605,899; 5,352,784; 5,446,153; and 5,482,936. Shen et al., U.S. Pat. Nos. 4,038, 396 and 4,131,677, describe certain oxazolo-and thiazolopyridines as having antiinflammatory, analgesic, and antipyretic properties.

SUMMARY OF THE INVENTION

The present invention provides compounds of the Formula I

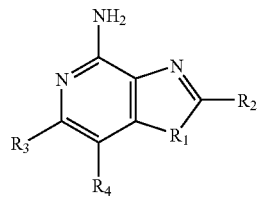

wherein:

$R_1$ is selected from the group consisting of oxygen, sulfur and selenium;

$R_2$ is selected from the group consisting of

-hydrogen;

-alkyl;

-alkyl-OH;

-haloalkyl;

-alkenyl;

-alkyl-X-alkyl;

-alkyl-X-alkenyl;

-alkenyl-X-alkyl;

-alkenyl-X-alkenyl;

-alkyl-N($R_5$)$_2$;

-alkyl-N$_3$;

-alkyl-O—C(O)—N($R_5$)$_2$;

-heterocyclyl;

-alkyl-X-heterocyclyl;

-alkenyl-X-heterocyclyl;

-aryl;

-alkyl-X-aryl;

-alkenyl-X-aryl;

-heteroaryl;

-alkyl-X-heteroaryl; and

-alkenyl-X-heteroaryl;

$R_3$ and $R_4$ are each independently:

-hydrogen;

—X-alkyl;

-halo;

-haloalkyl;

—N($R_5$)$_2$;

or when taken together, $R_3$ and $R_4$ form a fused aromatic, heteroaromatic, cycloalkyl or heterocyclic ring;

X is selected from the group consisting of —O—, —S—, —N$R_5$—, —C(O)—, —C(O)O—, —OC(O)—, and a bond; and each $R_5$ is independently H or $C_{1-8}$alkyl;

with the proviso that when $R_1$ is sulfur, $R_3$ is not —NH$_2$; or a pharmaceutically acceptable salt thereof.

As a second aspect, the present invention provides pharmaceutical compositions containing a therapeutically effective amount of a compound of Formula I(a) and a pharmaceutically acceptable vehicle:

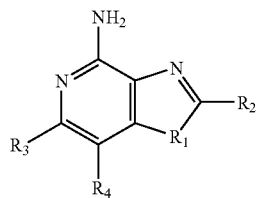

(I(a))

wherein:
R₁ is selected from the group consisting of oxygen, sulfur and selenium;
R₂ is selected from the group consisting of
-hydrogen;
-alkyl;
-alkyl-OH;
-haloalkyl;
-alkenyl;
-alkyl-X-alkyl;
-alkyl-X-alkenyl;
-alkenyl-X-alkyl;
-alkenyl-X-alkenyl;
-alkyl-N(R₅)₂;
-alkyl-N₃;
-alkyl-O—C(O)—N(R₅)₂;
-heterocyclyl;
-alkyl-X-heterocyclyl;
-alkenyl-X-heterocyclyl;
-aryl;
-alkyl-X-aryl;
-alkenyl-X-aryl;
-heteroaryl;
-alkyl-X-heteroaryl; and
-alkenyl-X-heteroaryl;
R₃ and R₄ are each independently:
-hydrogen;
—X-alkyl;
-halo;
-haloalkyl;
—N(R₅)₂;
or when taken together, R₃ and R₄ form a fused aromatic, heteroaromatic, cycloalkyl or heterocyclic ring;
X is selected from the group consisting of —O—, —S—, —NR₅—, —C(O)—, —C(O)O—, —OC(O)—, and a bond; and
each R₅ is independently H or C₁₋₈alkyl;
or a pharmaceutically acceptable salt thereof.

The compounds of Formula I(a) are useful in inducing the biosynthesis of certain cytokines in animals, including humans. Cytokines that may be induced by the compounds of the invention include but are not limited to, interferons, particularly interferon-α, and tumor necrosis factor-α. The invention therefore also provides a method of inducing cytokine biosynthesis in an animal by administering to the animal an effective amount of a composition comprising a compound of Formula I(a). Because of their ability to induce cytokine biosynthesis the compounds of the invention are useful in the treatment of a variety of conditions, including viral and neoplastic diseases, and the invention further provides a method of treating such conditions in a subject by administering a therapeutically effective amount of a composition comprising a compound of Formula I(a) to the subject.

As yet another aspect, the present invention provides intermediate compounds of Formula II

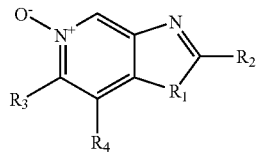

(II)

wherein:
R₁ is selected from the group consisting of oxygen, sulfur and selenium;
R₂ is selected from the group consisting of
-hydrogen;
-alkyl;
-alkyl-OH;
-haloalkyl;
-alkenyl;
-alkyl-X-alkyl;
-alkyl-X-alkenyl;
-alkenyl-X-alkyl;
-alkenyl-X-alkenyl;
-alkyl-N(R₅)₂;
-alkyl-N₃;
-alkyl-O—C(O)—N(R₅)₂;
-heterocyclyl;
-alkyl-X-heterocyclyl;
-alkenyl-X-heterocyclyl;
-aryl;
-alkyl-X-aryl;
-alkenyl-X-aryl;
-heteroaryl;
-alkyl-X-heteroaryl;
-alkenyl-X-heteroaryl;
—SO₂CH₃; and
—CH₂—O—C(O)—CH₃;
R₃ and R₄ are each independently:
-hydrogen;
—X-alkyl;
-halo;
-haloalkyl;
—N(R₅)₂;
or when taken together, R₃ and R₄ form a fused aromatic, heteroaromatic, cycloalkyl or heterocyclic ring;
X is selected from the group consisting of —O—, —S—, —NR₅—, —C(O)—, —C(O)O—, and a bond; and
each R₅ is independently H or C₁₋₈alkyl.

DETAILED DESCRIPTION OF THE INVENTION

This invention includes compounds of Formula I, pharmaceutical compositions containing compounds of Formula I(a) and therapeutic methods using compounds of Formula I(a) as well as intermediate compounds of Formula II that are used to prepare the compounds of Formulae I and I(a).

The terms "alkyl" and "alkenyl" as used herein refer to a straight or branched hydrocarbon group, or a cyclic group (i.e., cycloalkyl and cycloalkenyl) that contains from 1 to 20, preferably 1 to 10, more preferably 1 to 8 carbon atoms, unless otherwise specified. Typical alkyl groups are, for example, methyl, ethyl, n-propyl, isopropyl, n-butyl, isobutyl, sec-butyl, tert-butyl, n-pentyl, n-hexyl, n-heptyl, n-octyl, and the like. Exemplary cyclic groups include cyclopropyl, cyclopentyl, cyclohexyl, cyclohexenyl and adamantyl. The prefix "alk," when used, e.g. for "alkoxy" and the like, also has the same meaning.

The term "aryl" refers to a carbocyclic aromatic ring or ring system. The aryl group is preferably a six-membered ring, such as phenyl, or an aromatic polycyclic ring system, such as naphthyl. The most preferred aryl group is phenyl which may be unsubstituted or substituted by one or more substituents as defined below. Examples of other suitable aryl groups include biphenyl, fluorenyl and indenyl.

The term "heteroaryl" refers to an aromatic ring or ring system that contains one or more heteroatoms, in which the heteroatoms are selected from nitrogen, oxygen and sulfur. Suitable heteroaryl groups include furyl, thienyl, pyridyl, quinolinyl, tetrazolyl, imidazo, and so on. In the case where $R_3$ and $R_4$ are taken together and form a 5- or 6-membered heteroaromatic ring, the heteroatom is nitrogen, oxygen or sulfur and the ring may contain one or more of such atoms. Preferably, the heteroatom is nitrogen or sulfur. Preferred heteroaromatic rings formed by $R_3$ and $R_4$ are illustrated by the following formulae where the two lines indicate where they are fused.

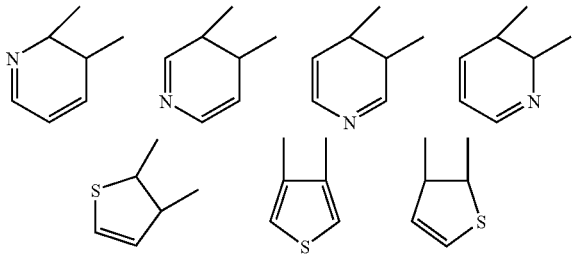

The terms "heterocyclic" and "heterocyclyl" refer to non-aromatic rings or ring systems that contain one or more ring heteroatoms (e.g., O, S, N). Exemplary heterocyclic groups include pyrrolidinyl, tetrahydrofuranyl, morpholinyl, piperidino, piperazino, thiazolidinyl, imidazolidinyl, and the like.

All of the above rings and ring systems can be unsubstituted or substituted by one or more substituents selected from the group consisting of alkyl, alkoxy, alkylthio, hydroxy, halogen, haloalkyl, polyhaloalkyl, perhaloalkyl (e.g., trifluoromethyl), trifluoroalkoxy (e.g., trifluoromethoxy), nitro, amino, alkylamino, dialkylamino, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile and alkoxycarbonyl. Preferred substituents are $C_{1-4}$ alkyl, $C_{1-4}$ alkoxy, halo, amino, alkylamino, dialkylamino, hydroxy, $C_{1-4}$ alkoxymethyl and trifluoromethyl.

The term "halo" refers to a halogen atom, such as, for example, fluorine, chlorine, bromine or iodine.

The invention is inclusive of the compounds described herein in any of their pharmaceutically acceptable forms, including isomers such as diastereomers and enantiomers, salts, solvates, polymorphs and the like.

As noted above, the compounds of Formula I and I(a) are capable of forming "pharmaceutically acceptable salt(s)." Pharmaceutically acceptable acid addition salts of the compounds of Formula I and I(a) include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, hydroxynaphthoate, xinafoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge SM, et al., "Pharmaceutical Salts," *J. Pharm. Sci.* 1977;66:1).

The acid addition salts of the compounds are prepared by contacting the free base form with a sufficient amount of the desired acid to produce the salt in the conventional manner. The free base form may be regenerated by contacting the salt form with a base and isolating the free base in the conventional manner.

Preferred compounds of Formula I and I(a) are those wherein $R_1$ is oxygen or sulfur. Preferred $R_2$ substituents include alkyl and alkoxyalkyl, with $C_{1-4}$ alkyl especially preferred.

It is preferred that $R_3$ and $R_4$ be taken together to form a fused benzene or pyridine ring that may be substituted or unsubstituted.

Most preferred compounds are those of the Formula III or IV

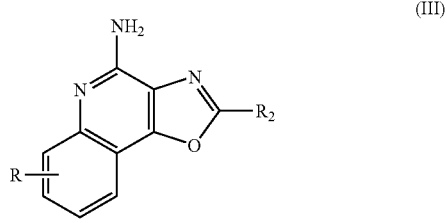

(III)

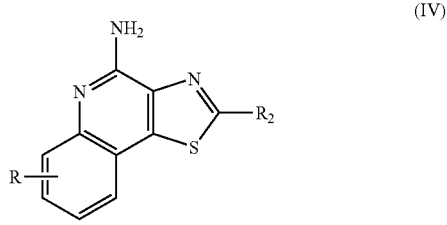

(IV)

wherein $R_2$ is defined above, and R is hydrogen, alkyl, alkoxy, alkylthio, hydroxy, halogen, haloalkyl, polyhaloalkyl, perhaloalkyl (e.g., trifluoromethyl), trifluoroalkoxy (e.g., trifluoromethoxy), nitro, amino, alkylamino, dialkylamino, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile and alkoxycarbonyl.

Exemplary compounds of the invention include:
  2-methylthiazolo[4,5-c]quinolin-4-amine;
  thiazolo[4,5-c]quinolin-4-amine;
  2-ethylthiazolo[4,5-c]quinolin-4-amine;
  2-propylthiazolo[4,5-c]quinolin-4-amine;
  2-pentylthiazolo[4,5-c]quinolin-4-amine;
  2-butylthiazolo[4,5-c]quinolin-4-amine;
  2-(1-methylethyl)thiazolo[4,5-c]quinolin-4-amine;
  2-(2-phenyl-1-ethenyl)thiazolo[4,5-c]quinolin-4-amine;
  2-(2-phenyl-1-ethyl)thiazolo[4,5-c]quinolin-4-amine;
  2-(4-aminothiazolo[4,5-c]quinolin-2-yl)-1,1-dimethylethyl carbamate;

2-(ethoxymethyl)thiazolo[4,5-c]quinolin-4-amine;
2-(methoxymethyl)thiazolo[4,5-c]quinolin-4-amine;
2-(2-methylpropyl)thiazolo[4,5-c]quinolin-4-amine;
2-benzylthiazolo[4,5-c]quinolin-4-amine;
8-methyl-2-propylthiazolo[4,5-c]quinolin-4-amine;
(4-aminothiazolo[4,5-c]quinolin-2-yl)methanol;
2-methyloxazolo[4,5-c]quinolin-4-amine;
2-ethyloxazolo[4,5-c]quinolin-4-amine;
2-butyloxazolo[4,5-c]quinolin-4-amine;
2-propylthiazolo [4,5-c]quinolin-4,8-diamine;
2-propyloxazolo [4,5-c]quinolin-4-amine;
8-bromo-2-propylthiazolo[4,5-c]quinolin-4-amine;
7-methyl-2-propylthiazolo[4,5-c]quinolin-4-amine;
2-butyl-7-methyloxazolo[4,5-c]quinolin-4-amine;
7-methyl-2-propyloxazolo[4,5-c]quinolin-4-amine;
7-fluoro-2-propyloxazolo[4,5-c]quinolin-4-amine;
7-fluoro-2-propylthiazolo[4,5-c]quinolin-4-amine;
2-propyl-7-(trifluoromethyl)thiazolo[4,5-c]quinolin-4-amine;
2-(4-morpholino)thiazolo[4,5-c]quinolin-4-amine;
2-(1-pyrrolidino)thiazolo[4,5-c]quinolin-4-amine;
2-butylthiazolo[4,5-c][1,5]naphthyridin-4-amine;
2-propylthiazolo[4,5-c][1,5]naphthyridin-4-amine;
7-chloro-2-propylthiazolo[4,5-c]quinolin-4-amine;
7-methoxy-2-propylthiazolo[4,5-c]quinolin-4-amine;
and pharmaceutically acceptable salts thereof, particularly the hydrochloride salts thereof.

Preparation of the Compounds

Compounds of the invention can be prepared according to Reaction Scheme I wherein $R_1$, $R_2$, $R_3$ and $R_4$ are as defined above.

In step (1) of Reaction Scheme I a compound of Formula V is reacted with a carboxylic acid or an equivalent thereof to provide a compound of Formula VI. Suitable equivalents to carboxylic acid include acid anhydrides, acid chlorides, orthoesters and 1,1-dialkoxyalkanoates. The carboxylic acid or equivalent is selected such that it will provide the desired $R_2$ substituent in a compound of Formula VI. For example, triethyl orthoformate will provide a compound of Formula VI where $R_2$ is hydrogen and acetic anhydride will provide a compound of Formula VI where $R_2$ is methyl. The reaction can be run in the absence of solvent, in the presence of an acid such as polyphosphoric acid, or preferably in the presence of a carboxylic acid of the formula $R_2C(O)OH$. The reaction is run with sufficient heating to drive off any alcohol or water formed as a byproduct of the reaction. The compounds of Formula V are known or may be prepared using conventional methods (see for example, Bachman et. al., *Journal of the American Chemical Society*, 69, pp 365–371 (1947); Ambrogi et. al., *Synthesis*, pp. 656–658 (1992); Adler et. al., *Journal of the Chemical Society*, pp.1794–1797 (1960); Süs et. al., *Justus Liebigs Annalen der Chemie*, 583, pp. 150–160 (1953); and Süs et. al., *Justus Liebigs Annalen der Chemie*, 593, pp. 91–126 (1955).

In step (2) of Reaction Scheme I a compound of Formula VI is oxidized to provide an N-oxide of Formula II. The oxidation is carried out using a conventional oxidizing agent that is capable of forming N-oxides. Preferred reaction conditions involve reacting a solution of a compound of Formula VI in chloroform with 3-chloroperoxybenzoic acid at ambient conditions. Alternatively the oxidation may be carried out using peracetic acid in a suitable solvent such as ethyl or methyl acetate.

In step (3) of Reaction Scheme I an N-oxide of Formula II is aminated to provide a compound of Formula I. Step (3) involves (i) reacting a compound of Formula II with an acylating agent and then (ii) reacting the product with an aminating agent. Part (i) of step (3) involves reacting an N-oxide of Formula II with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (3) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving or suspending the N-oxide of Formula II in an inert solvent such as dichloromethane or chloroform, adding the aminating agent to the solution or suspension, and then slowly adding the acylating agent. The product or a pharmaceutically acceptable salt thereof can be isolated using conventional methods.

Alternatively, step (3) can be carried out by (i) reacting an N-oxide of Formula II with an isocyanate and then (ii) hydrolyzing the resulting product. Part (i) involves reacting the N-oxide with an isocyanate wherein the isocyanato group is bonded to a carbonyl group. Preferred isocyanates include trichloroacetyl isocyanante and aroyl isocyanates such as benzoyl isocyanate. The reaction of the isocyanate with the N-oxide is carried out under substantially anhydrous conditions by adding the isocyanate to a solution of the N-oxide in an inert solvent such as dichloromethane. Part (ii) involves hydrolysis of the product from part (i). The hydrolysis can be carried out by conventional methods such as heating in the presence of water or a lower alkanol optionally in the presence of a catalyst such as an alkali metal lower alkoxide or ammonia.

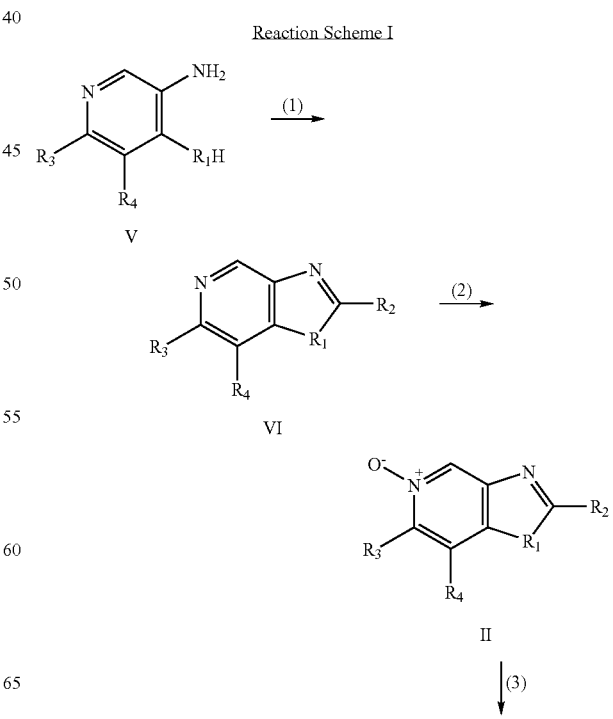

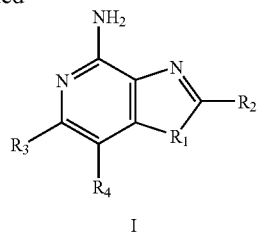

I

Compounds of the invention wherein $R_1$ is oxygen or sulfur and $R_3$ and $R_4$ together form an optionally substituted aromatic ring can be prepared according to Reaction Scheme II wherein R and $R_2$ are as defined above.

In step (1) of Reaction Scheme II a 3-aminoquinolin-4-ol or 3-aminoquinolin-4-thiol of Formula VII is reacted with a carboxylic acid or an equivalent thereof to provide an oxazolo- or thiazolo[4,5-c]quinoline of Formula VIII. Suitable equivalents to carboxylic acid include acid anhydrides, acid chlorides, orthoesters and 1,1-dialkoxyalkanoates. The carboxylic acid or equivalent is selected such that it will provide the desired $R_2$ substituent in a compound of Formula VIII. For example, triethyl orthoformate will provide a compound of Formula VIII where $R_2$ is hydrogen and acetic anhydride will provide a compound of Formula VIII where $R_2$ is methyl. The reaction can be run in the absence of solvent, in the presence of an acid such as polyphosphoric acid, or preferably in the presence of a carboxylic acid of the formula $R_2C(O)OH$. The reaction is run with sufficient heating to drive off any alcohol or water formed as a byproduct of the reaction. The 3-aminoquinolin-4-ols and 3-aminoquinolin-4-thiols of Formula VII are known or may be prepared using known methods.

In step (2) of Reaction Scheme II an oxazolo- or thiazolo[4,5-c]quinoline of Formula VIII is oxidized to provide an oxazolo- or thiazolo[4,5-c]quinolin-5N-oxide of Formula IX which is a subgenus of Formula II. The oxidation is carried out using a conventional oxidizing agent that is capable of forming N-oxides. Preferred reaction conditions involve reacting a solution of a compound of Formula VIII in chloroform with 3-chloroperoxybenzoic acid at ambient conditions. Alternatively the oxidation may be carried out using peracetic acid in a suitable solvent such as ethyl or methyl acetate.

In step (3) of Reaction Scheme II an N-oxide of Formula IX is aminated to provide an oxazolo[4,5-c]quinolin-4-amine of Formula III or a thiazolo[4,5-c]quinolin-4-amine of Formula IV both of which are subgenera of Formula I. Step (3) involves (i) reacting a compound of Formula IX with an acylating agent and then (ii) reacting the product with an aminating agent. Part (i) of step (3) involves reacting an N-oxide of Formula IX with an acylating agent. Suitable acylating agents include alkyl- or arylsulfonyl chlorides (e.g., benzenesulfonyl chloride, methanesulfonyl chloride, p-toluenesulfonyl chloride). Arylsulfonyl chlorides are preferred. Para-toluenesulfonyl chloride is most preferred. Part (ii) of step (3) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving or suspending the N-oxide of Formula IX in an inert solvent such as dichloromethane or chloroform, adding the aminating agent to the solution or suspension, and then slowly adding the acylating agent. The product or a pharmaceutically acceptable salt thereof can be isolated using conventional methods.

Alternatively, step (3) can be carried out by (i) reacting an N-oxide of Formula IX with an isocyanate and then (ii) hydrolyzing the resulting product. Part (i) involves reacting the N-oxide with an isocyanate wherein the isocyanato group is bonded to a carbonyl group. Preferred isocyanates include trichloroacetyl isocyanante and aroyl isocyanates such as benzoyl isocyanate. The reaction of the isocyanate with the N-oxide is carried out under substantially anhydrous conditions by adding the isocyanate to a solution of the N-oxide in an inert solvent such as dichloromethane. Part (ii) involves hydrolysis of the product from part (i). The hydrolysis can be carried out by conventional methods such as heating in the presence of water or a lower alkanol optionally in the presence of a catalyst such as an alkali metal lower alkoxide or ammonia.

Reaction Scheme II

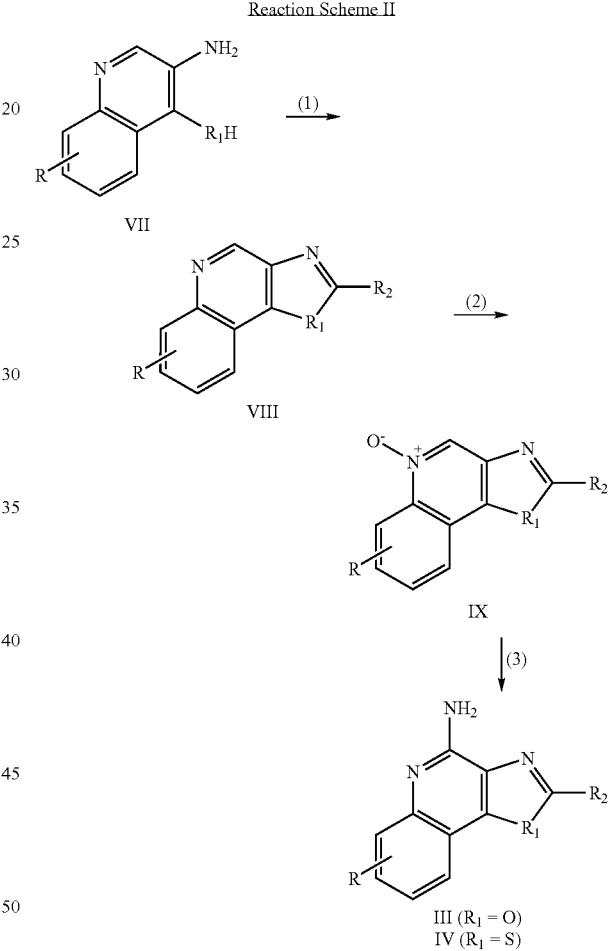

III ($R_1 = O$)
IV ($R_1 = S$)

Compounds of the invention wherein $R_1$ is sulfur can also be prepared according to Reaction Scheme III wherein $R_2$, $R_3$ and $R_4$ are as defined above.

In step (1) of Reaction Scheme III a compound of Formula X is reacted with an acyl halide of formula $R_2C(O)Z$ wherein $R_2$ is as defined above and Z is chloro or bromo to provide an amide of Formula XI. The reaction can be carried out by adding the acyl halide in a controlled fashion (e.g., dropwise) to a solution or suspension of a compound of Formula X in a suitable solvent such as pyridine or dichloromethane in the presence of a tertiary amine.

In step (2) of Reaction Scheme III an amide of Formula XI is reacted with phosphorous pentasulfide to provide a compound of Formula XII. The reaction can be carried out by adding phosphorous pentasulfide to a solution or suspension of a compound of Formula XI in a suitable solvent such as pyridine and heating the resulting mixture.

Steps (3) and (4) of Reaction Scheme III can be carried out in the same manner as steps (2) and (3) of Reaction Scheme I respectively to provide an N-oxide of Formula XIII which is a subgenus of Formula II and a compound of Formula XIV which is a subgenus of Formula I respectively.

compound of Formula XVI in a suitable solvent such as pyridine and heating the resulting mixture.

Steps (3) and (4) of Reaction Scheme IV can be carried out in the same manner as steps (2) and (3) of Reaction Scheme II respectively to provide a thiazolo[4,5-c]quinolin-5N-oxide of Formula XVIII which is a subgenus of Formula II and a thiazolo[4,5-c]quinolin-4-amine of Formula IV which is a subgenus of Formula I respectively.

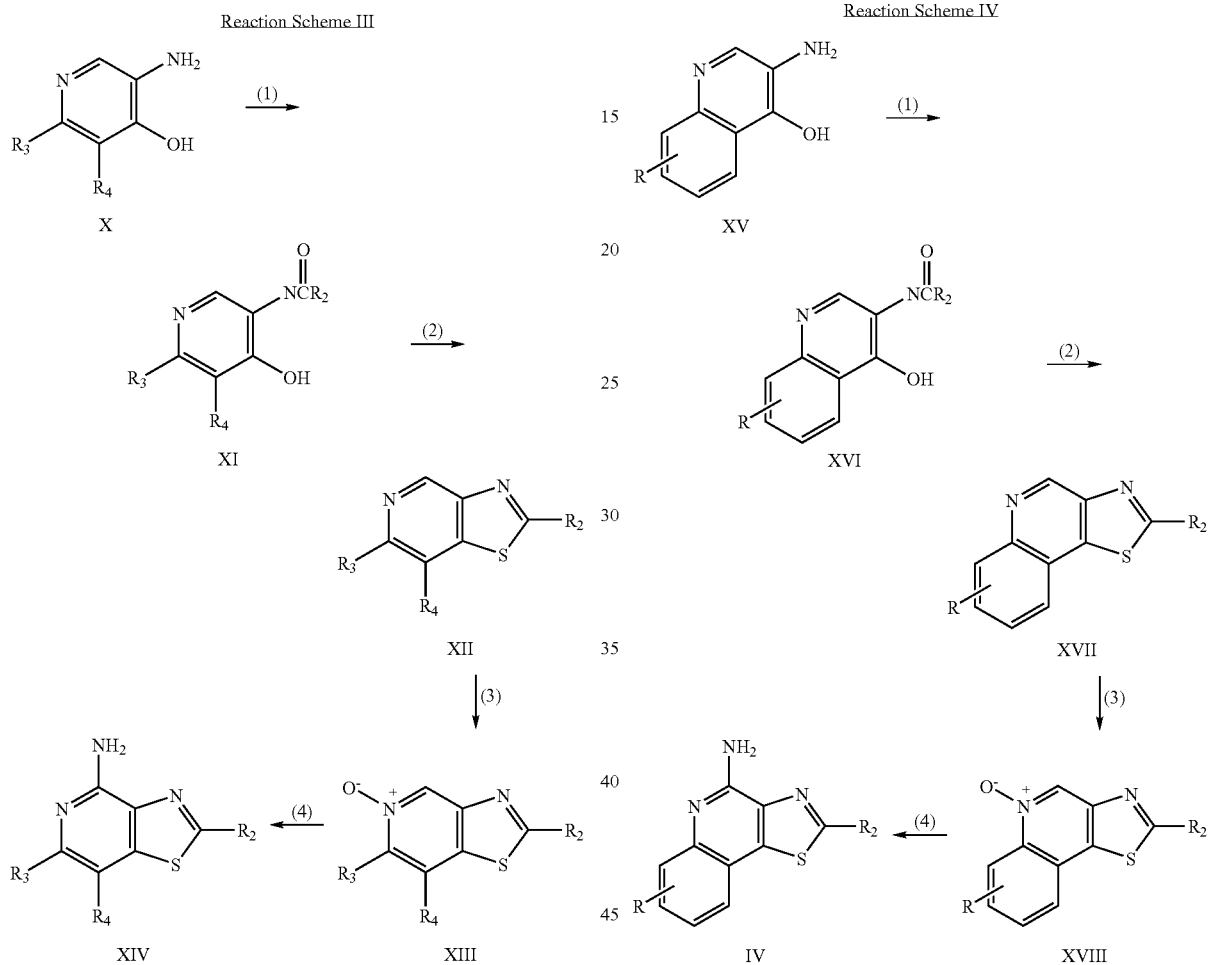

Compounds of the invention wherein $R_1$ is sulfur and $R_3$ and $R_4$ together form an optionally substituted aromatic ring can also be prepared according to Reaction Scheme IV wherein R and $R_2$ are as defined above.

In step (1) of Reaction Scheme IV a 3-aminoquinolin-4-ol of Formula XV is reacted with an acyl halide of formula $R_2C(O)Z$ wherein $R_2$ is as defined above and Z is chloro or bromo to provide an N-(4-hydroxyquinolin-3-yl)amide of Formula XVI. The reaction can be carried out by adding the acyl halide in a controlled fashion (e.g., dropwise) to a solution or suspension of a compound of Formula XV in a suitable solvent such as dichloromethane in the presence of a tertiary amine.

In step (2) of Reaction Scheme IV an N-(4-hydroxyquinolin-3-yl)amide of Formula XVI is reacted with phosphorous pentasulfide to provide a thiazolo[4,5-c]quinoline of Formula XVII. The reaction can be carried out by adding phosphorous pentasulfide to a solution or suspension of a Substituents at the 2-position can be introduced by reacting a compound of Formula XIX

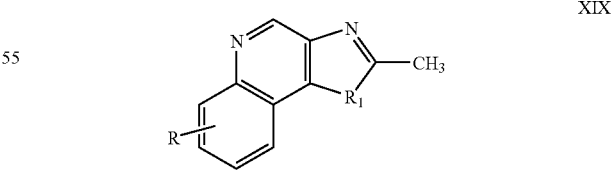

wherein $R_1$ is oxygen or sulfur and R is as defined above, with a lithiating agent such as lithium diisopropylamide or n-butyllithium in a polar aprotic solvent to provide a compound lithiated on the 2-methyl group. The lithiated compound can then be reacted with an appropriate reagent containing a leaving group capable of being displaced by the lithiated 2-methyl group. Examples of suitable reagents include halides such as methyl iodide or chloromethylmethylether, aldehydes such as benzaldehyde, and ketones such as acetone. The compounds can then be oxidized and aminated using the methods described above to provide compounds of Formulas III or IV.

Some compounds of Formula I may be prepared directly from other compounds of Formula I. For example, nitration of 2-propylthiazolo[4,5-c]quinolin-4-amine provides 8-nitro-2-propylthiazolo[4,5-c]quinolin-4-amine and the reduction of the nitro compound provides 2-propylthiazolo[4,5-c]quinoline-4,8-diamine.

Pharmaceutical Compositions and Biological Activity

Pharmaceutical compositions of the invention contain a therapeutically effective amount of a compound of Formula I(a) together with a pharmaceutically acceptable carrier.

As used herein, the term "a therapeutically effective amount" means an amount of the compound sufficient to induce a desired therapeutic effect, such as cytokine biosynthesis, antitumor activity and/or antiviral activity. Although the exact amount of active compound used in a pharmaceutical composition of the invention will vary according to factors known to those of skill in the art, such as the physical and chemical nature of the compound as well as the nature of the carrier, the intended dosing regimen and the condition to be treated, it is anticipated that the compositions of the invention will contain sufficient active ingredient to provide a dose of about 100 ng/kg to about 50 mg/kg, preferably about 10 μg/kg to about 5 mg/kg of the compound to the subject. Any of the conventional dosage forms may be used, such as tablets, lozenges, parenteral formulations, syrups, creams, ointments, aerosol formulations, transdermal patches, transmucosal patches and so on. The dosage form used will also depend on the characteristics of the compound to be administered. For example, certain compounds of Formula I(a), especially those wherein $R_1$ is sulfur, tend to have relatively low oral bioavailability and are rapidly metabolized when they enter the bloodstream. These properties make such compounds particularly well suited for treatment of conditions where topical administration of an immune response modifying compound is desirable, such as asthma, basal cell carcinoma, cervical intraepithelial neoplasia and so on.

The compounds of the invention have been shown to induce the production of certain cytokines in experiments performed according to the Test Method set forth below. These results indicate that the compounds are useful as immune response modifiers that can modulate the immune response in a number of different ways, rendering them useful in the treatment of a variety of disorders.

Cytokines that are induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, 6, 10 and 12, and a variety of other cytokines. Among other effects, cytokines inhibit virus production and tumor cell growth, making the compounds useful in the treatment of tumors and viral diseases.

In addition to the ability to induce the production of cytokines, the compounds of the invention affect other aspects of the innate immune response. For example, natural killer cell activity may be stimulated, which effect may be due to cytokine induction. The compounds may also activate macrophages, which in turn stimulates secretion of nitric oxide and the production of additional cytokines. Further, the compounds may cause proliferation and differentiation of B-lymphocytes and may be useful in the in vitro maturation of dendritic cells.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or down regulation of the Th2 response is desired. In view of the ability of compounds of Formula Ia to inhibit the Th2 immune response, the compounds are expected to be useful in the treatment of atopy, e.g., atopic dermatitis, asthma, allergy, allergic rhinits, and systemic lupus erythematosis; as a vaccine adjuvant for the enhancement of cell mediated immunity; and possibly as a treatment for recurrent fungal diseases and chlamydia.

The immune response modifying effects of the compounds make them useful in the treatment of a wide variety of conditions. Because of their ability to induce cytokines such as IFN-α and/or TNF-α, the compounds are particularly useful in the treatment of viral diseases and tumors. This immunomodulating activity suggests that compounds of the invention are useful in treating diseases such as, but not limited to, viral diseases e.g., genital warts, common warts, plantar warts, Hepatitis B, Hepatits C, Herpes Simplex Type I and Type II, molluscum contagiosm, HIV, CMV, VZV, cervical intraepithelial neoplasia, human papillomavirus and associated neoplasias; fungal diseases, e.g., candida, aspergillus, cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g., pneumocystis carnii, cryptospordiosis, histoplasmosis, toxoplasmosis, trypanosome infection, leishmaniasis; and bacterial infections, e.g., tuberculosis, mycobacterium avium. Additional diseases or conditions that can be treated using the compounds of the invention include eczema, eosinophilia, essential thrombocythaemia, leprosy, multiple sclerosis, Ommen's syndrome, rheumatoid arthritis, systemic lupus erythematosis, discoid lupus, Bowen's disease, Bowenoid papulosis, and to enhance or stimulate the healing of wounds, including chronic wounds.

Accordingly, the invention provides a method of inducing cytokine biosynthesis in an animal comprising administering an effective amount of a compound of Formula Ia to the animal. An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1,6,10 and 12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal comprising administering an effective amount of a compound of Formula Ia to the animal. An amount effective to treat or inhibit a viral infection is an amount that will cause a reduction in one or more of the manifestations of viral infection, such as viral lesions, viral load, rate of virus production, and mortality as compared to

EXAMPLES

Example 1

2-Methylthiazolo[4,5-c]quinoline-5N-oxide

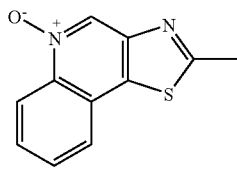

Part A

A suspension of 3-aminoquinoline-4-thiol (about 12 g) in a mixture of acetic anhydride (150 mL) and acetic acid (300 mL) was heated at reflux overnight. The reaction mixture was filtered to remove a fine solid. The filtrate was evaporated under vacuum. The residue was diluted with ethanol then refluxed for 30 minutes. The solution was concentrated under vacuum and the residue diluted with water. The aqueous residue was made basic with sodium hydroxide and then extracted with diethyl ether. The ether extracts were combined, dried over magnesium sulfate and filtered. The filtrate was evaporated to provide 12.8 g of crude product. A sample (800 mg) was recrystallized from hexane to provide 2-methylthiazolo[4,5-c]quinoline as yellow needles, m.p. 95.5–97.5° C. Analysis: Calculated for $C_{11}H_8N_2S$: % C, 65.97; % H, 4.03; % N, 13.99; Found: % C, 65.96; % H, 4.16; % N 14.08.

Part B

2-Methylthiazolo[4,5-c]quinoline (5.0 g, 25 mmol), 3-chloroperoxybenzoic acid (9.5 g of 50–60%), and dichloromethane (150 mL) were combined and stirred at ambient temperature for 3 hours. The reaction solution was diluted with dichloromethane (300 mL) and then extracted with aqueous sodium carbonate to remove the acids. The organic layer was washed with water, diluted with ethyl acetate to remove cloudiness, dried over magnesium sulfate, and then concentrated under vacuum to provide 4.5 g of crude product. A small portion was recrystallized from methanol to provide yellow needles of 2-methylthiazolo[4,5-c]quinoline-5N-oxide hydrate, m.p. 150–160° C. Analysis: Calculated for $C_{11}H_8N_2OS+0.75H_2O$: % C, 57.50; % H, 4.17; % N, 12.19; Found: % C, 57.58; % H, 4.10; % N, 11.93.

Example 2

2-Methylthiazolo[4,5-c]quinolin-4-amine

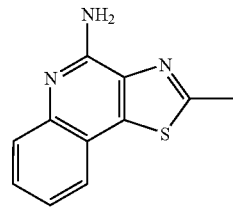

2-Methylthiazolo[4,5-c]quinoline-5N-oxide (1.5 g, 6.9 mmol) was added to a mixture of dichloromethane (10 mL) and ammonium hydroxide (25 mL). A solution of tosyl chloride (2.0 g, 10.4 mmol) in dichloromethane (10 mL) was added with vigorous stirring to the reaction mixture. The reaction was refluxed with additional dichloromethane and ammonium hydroxide being added until thin layer chromatography indicated that the reaction was complete. The dichloromethane was distilled from the mixture and yellow product was filtered from the aqueous residue. The solid was washed with water and then dried to provide 1.2 g of crude product. The solid was dissolved in dilute hydrochloric acid. The solution was treated with charcoal and then filtered. The filtrate was made basic with dilute sodium hydroxide. The resulting precipitate was isolated by filtration, washed with water, dried and then recrystallized from methanol/dichloromethane to provide 0.46 g of 2-methylthiazolo[4,5-c]quinolin-4-amine as a white powder, m.p. 184–187° C. Analysis: Calculated for $C_{11}H_9N_3S$: % C, 61.37; % H, 4.21; % N, 19.52; Found: % C, 61.32; % H, 4.52; % N, 19.68.

Example 3

2-Methylthiazolo[4,5-c]quinolin-4-amine
Alternative Synthesis

Trichloroacetyl isocyanate (2.0 mL, 16.8 mmol) was added to a suspension of 2-methylthiazolo[4,5-c]quinoline-5N-oxide (3.03 g, 14.0 mmol) in dichloromethane (150 mL). The reaction mixture was stirred at ambient temperature for about 50 minutes. The dichloromethane was concentrated under vacuum to provide crude N-(2-methylthiazolo[4,5-c]quinolin-4-yl)trichloroacetamide. The amide was dissolved in methanol and then sodium methoxide (1 mL of 25% sodium methoxide in methanol) was added. The reaction was heated at reflux for 40 minutes then the methanol was evaporated under vacuum. The resulting brown solid was washed with water and dried to provide 2.85 g of crude product. This material was treated with charcoal and then recrystallized from ethyl acetate to provide 2-methylthiazolo[4,5-c]quinolin-4-amine as a solid, m.p. 184–186° C. Analysis: Calculated for $C_{11}H_9N_3S$: % C, 61.37; % H, 4.21; % N, 19.52; Found % C, 61.48; % H, 4.17; % N, 19.60.

Example 4

2-Methylthiazolo[4,5-c]quinolin-4-amine
Hydrochloride

Concentrated hydrochloric acid (0.2 mL of 12.1M) was added to a solution of 2-methylthiazolo[4,5-c]quinolin-4- amine (0.5 g) in methanol (15 mL). Isopropanol (15 mL) was added and then the reaction mixture was heated at reflux to remove the majority of the methanol. The resulting precipitate was isolated by filtration, washed with isopropanol and dried to provide 2-methylthiazolo[4,5-c]quinolin-4-amine hydrochloride as a solid, m.p. 323–325° C. Analysis: Calculated for $C_{11}H_9N_3S$ HCl: % C, 52.48; % H, 4.00; % N, 16.69; Found: % C, 52.46; % H, 4.08; % N, 16.52.

Example 5

Thiazolo[4,5-c]quinolin-4-amine Hydrochloride Hydrate

Part A

3-Aminoquinoline-2-thiol (about 18.5 g) was added to triethyl orthoformate (26.0 mL). The reaction mixture was heated on a steam bath for 20 minutes. Formic acid (400 mL) was added and the reaction mixture was heated at reflux overnight. The bulk of the formic acid was evaporated under vacuum. The residue was combined with ethanol and heated at reflux for 30 minutes. The ethanol was evaporated under vacuum. The residue was suspended in water and then made basic by adding sodium hydroxide. A precipitate formed. The solid was extracted with several portions of dichloromethane. The extracts were combined, dried over magnesium sulfate and then concentrated to provide a yellow solid which was recrystallized from hexanes to provide 13.1 g of thiazolo[4,5-c]quinoline as a yellow crystalline solid, m.p. 104–106° C.

Part B

Peracetic acid (21 mL of 32% in acetic acid, 100 mmol) was added to a suspension of thiazolo[4,5-c]quinoline (12.5 g, 67 mmol) in methyl acetate (300 mL). The reaction mixture was heated at reflux overnight and then cooled to ambient temperature. A precipitate was isolated by filtration and then suspended in water (100 mL). Aqueous sodium bicarbonate (100 mL) was added to the suspension and the mixture was stirred for one hour. The solid thiazolo[4,5-c]quinoline-5N-oxide was isolated by filtration, washed with water and dried.

Part C

Trichloroacetyl isocyanate (0.72 mL, 6.0 mmol) was added to a suspension of thiazolo[4,5-c]quinoline-5N-oxide (1.10 g, 5.4 mmol) in dichloromethane (100 mL). The reaction mixture was stirred at ambient temperature for 45 minutes and then the dichloromethane was evaporated under vacuum to provide crude N-(thiazolo[4,5-c]quinolin-4-yl) trichloroacetamide. The amide was combined with 2M ammonia in methanol and stirred at ambient temperature for 2 hours. The methanol was evaporated under vacuum. The residue was suspended in water, combined with sodium carbonate and then stirred for 10 minutes. A brown solid was collected, washed with water and dried. The solid was suspended in water, hydrochloric acid (100 mL of 6N) was added and the mixture was heated on a steam bath. The mixture was filtered; then the filtrate was allowed to slowly cool to ambient temperature. The resulting precipitate was isolated by filtration and then dried to provide 0.75 g of brown needles. This material was dissolved in water (100 mL) with heating. Charcoal was added and the mixture was heated with stirring for 5 minutes. The mixture was filtered through a layer of Celite® filter agent. The filtrate was heated on a steam bath to remove most of the water and then allowed to cool to ambient temperature. The precipitate was isolated by filtration and dried to provide 0.30 g of thiazolo [4,5-c]quinolin-4-amine hydrochloride hydrate as a white crystalline solid, m.p. 284–285° C. Analysis: Calculated for $C_{10}H_7N_3S$ HCl $H_2O$: % C, 46.97; % H, 3.94; % N, 16.43; Found: % C, 46.96; % H, 3.99; % N, 16.34.

Example 6

Thiazolo[4,5-c]quinolin-4-amine

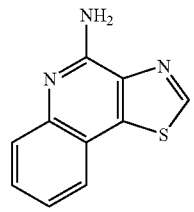

Part A

Thiazolo[4,5-c]quinoline-2-thiol (8.7 g, 0.04 mole) was suspended in a solution of sodium hydroxide (1.4 g, 0.04 mole) in water. A few drops of 50% sodium hydroxide were added to the suspension until most of the solid dissolved. Hydrogen peroxide (13.5 mL of 30%, 0.08 mole) was added dropwise over a period of 30 minutes while maintaining the temperature of the reaction mixture at 25–35° C. with a cold water bath. The bath was removed and the reaction mixture was stirred for 15 minutes. Sulfuric acid (2.5 g of 95.98%) was added dropwise to the reaction mixture. After 30 minutes the reaction was made basic (pH 9–9.5) with 50% sodium hydroxide. The reaction mixture was acidified (pH 2.5) with hydrochloric acid, a tan solid precipitated. The mixture was then heated on a steam bath for 15 minutes and the precipitate dissolved. The solution was allowed to cool to ambient temperature and a precipitate formed. The mixture was made basic (pH 9) with 50% sodium hydroxide. The resulting oily product was extracted with ethyl acetate. The extracts were combined, washed with water, dried over magnesium sulfate and then concentrated under vacuum to provide 3.3 g of thiazolo[4,5-c]quinoline as a tan solid, m.p. 104.4–105° C. Analysis: Calculated for $C_{10}H_6N_2S$: % C, 64.19; % H, 3.25; % N, 15.04; Found: % C, 64.15; % H, 3.26; % N, 14.9.

Part B

Peracetic acid (4.7 mL of 32%) was added to a solution of thiazolo[4,5-c]quinoline (2.8 g) in methyl acetate. A precipitate formed after several minutes. The reaction mixture was heated to reflux and then diluted with an additional 10 mL of methyl acetate. Most of the precipitate dissolved. After 1 hour an additional 3.1 mL of peracetic acid was added. The reaction mixture was heated overnight and then allowed to cool to ambient temperature. The methyl acetate and acetic acid were azeotroped off with heptane. The resulting oily product was suspended in water. The mixture was made basic with saturated sodium bicarbonate and then extracted with ethyl acetate. The ethyl acetate extracts were combined, washed with water, dried over magnesium sulfate and then concentrated under vacuum to provide 0.6 g of thiazolo[4,5-c]quinoline-5N-oxide as an orange solid, m.p. 178.4° C. (dec).

Part C

A solution of tosyl chloride (0.3 g) in water was added dropwise to a cooled (5° C.) suspension of thiazolo[4,5-c]quinoline-5N-oxide (0.3 g) in a mixture of ammonium hydroxide (5 mL) and dichloromethane (50 mL). The temperature was maintained at 4–6° C. throughout the addition. After the addition was complete the reaction mixture was stirred at ambient temperature for 4 hours. Analysis by thin layer chromatography showed the presence of starting material. The reaction mixture was cooled and 1 equivalent of tosyl chloride was added. The reaction mixture was stirred at ambient temperature for 20 hours. The dichloromethane was evaporated under vacuum. The residue was slurried in a small amount of water. The mixture was filtered. The isolated solid was washed with water, dried and then recrystallized from isopropanol to provide 0.2 g of thiazolo[4,5-c]quinolin-4-amine as an orange powder, m.p. 172.4° C. (dec). Analysis: Calculated for $C_{10}H_7N_3S$: % C, 59.68; % H, 3.50; % N, 20.88; Found: % C, 59.82; % H, 3.20; % N, 19.50.

Example 7

2-Ethylthiazolo[4,5-c]quinoline-5N-oxide

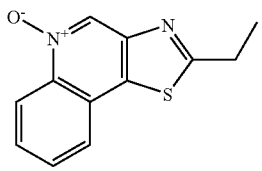

Part A

Under a nitrogen atmosphere, 2-methylthiazolo[4,5-c]quinoline (1.0 g, 10.0 mmol, Example 2 or 3) was placed in a dried flask. Anhydrous tetrahydrofuran (50 mL) was added and the reaction mixture was cooled to −78° C. with a dry ice bath. Lithium diisopropylamide (6.7 mL of 1.5 M in hexane, 10.0 mmol) was added dropwise. 30 minutes later methyl iodide (0.95 mL, 15.0 mmol) was added. After 40 minutes the reaction was allowed to warm to ambient temperature. The reaction mixture was quenched with water and then extracted with diethyl ether (250 mL). The extract was washed with water (3×100 mL), dried over magnesium sulfate and then concentrated under vacuum to provide 2.8 g of a brown oil. This material was purified using high performance liquid chromatography eluting with 3:1 hexane:ethyl acetate to provide 1.47 g of 2-ethylthiazolo[4,5-c]quinoline as a yellow oil.

Part B

3-Chloroperoxybenzoic acid (0.44 g) was added to a solution of 2-ethylthiazolo[4,5-c]quinoline (0.53 g) in chloroform (20 mL). The reaction mixture was stirred at ambient temperature for 2 hours and then diluted with dichloromethane (20 mL), washed with sodium bicarbonate, washed with water (3×100 mL), dried over magnesium sulfate and then concentrated under vacuum. The resulting yellow solid was recrystallized from ethyl acetate to provide 0.32 g of 2-ethylthiazolo[4,5-c]quinoline-5N-oxide as a solid, m.p. 128° C. Analysis: Calculated for $C_{12}H_{10}N_2OS$: % C, 62.59% H, 4.38; % N, 12.16; Found: % C, 62.59; % H, 4.27; % N, 12.12.

Example 8

2-Ethylthiazolo[4,5-c]quinolin-4-amine

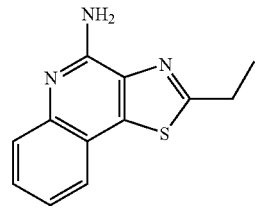

Part A

Trichloroacetyl isocyanate (0.51 mL, 4.3 mmol) was added to a suspension of 2-ethylthiazolo[4,5-c]quinoline-5N-oxide (0.90 g, 3.9 mmol) in dichloromethane (60 mL). The reaction mixture was stirred at ambient temperature for 30 minutes and then concentrated under vacuum to provide 1.80 g of N-(2-ethylthiazolo[4,5-c]quinolin-4-yl)trichloroacetamide as a yellow solid.

Part B

N-(2-ethylthiazolo[4,5-c]quinolin-4-yl)trichloroacetamide (0.40 g) was suspended in a solution of ammonia in methanol (20 mL of 2M) and then stirred at ambient temperature for 30 minutes. The reaction mixture was concentrated under vacuum. The residue was washed with water and then dried to provide 0.19 g of crude product which was recrystallized from ethyl acetate/hexane to provide 2-ethylthiazolo[4,5-c]quinolin-4-amine as tan needles, m.p. 170–172° C. Analysis: Calculated for $C_{12}H_{11}N_3S$: % C, 62.85; % H, 4.83; % N, 18.32; Found: % C, 62.58; % H, 4.78; % N, 18.08.

Example 9

2-Ethylthiazolo[4,5-c]quinolin-4-amine Alternative Synthesis

Part A

Propionyl anhydride (20 mL) was added to a suspension of 3-amino-quinoline-4-thiol (15 g) in propionic acid (100 mL). The reaction mixture was heated at reflux overnight and then filtered to remove a precipitate. The filtrate was concentrated under vacuum. The residue was taken up in dichloromethane (200 mL), washed with sodium bicarbonate then with water, and then dried over magnesium sulfate. The solution was filtered through a layer of silica gel eluting first with 1:1 ethyl acetate:hexane and then with ethyl acetate. The filtrate was evaporated to provide 2.6 g of 2-ethylthiazolo[4,5-c]quinoline as a yellow oil.

Part B

Peracetic acid (7.4 mL of 32%) was added to a solution of 2-ethylthiazolo[4,5-c]quinoline (5 g) in ethyl acetate (100 mL). The reaction mixture was stirred at ambient temperature for 2 days. The resulting precipitate was isolated by filtration, washed with hexane and dried to provide 3.4 g of 2-ethylthiazolo[4,5-c]quinoline-5N-oxide.

Part C

Trichloroacetyl isocyanate (6.5 mL, 54 mmol) was added to a suspension of 2-ethylthiazolo[4,5-c]quinoline-5N-oxide (9.0 g, 39.1 mmol) in dichloromethane (500 mL). The reaction mixture was stirred at ambient temperature for 2 hours and then concentrated under vacuum to provide crude N-(2-ethylthiazolo[4,5-c]quinolin-4-yl)trichloroacetamide. This material was added to a solution of ammonia in methanol (500 mL of 2M) and stirred at ambient temperature for about 2 hours. The reaction mixture was concentrated under vacuum. The residue was taken up in dichloromethane, washed with sodium bicarbonate (2×150 mL) then with water (3×150 mL), dried over magnesium sulfate and then concentrated under vacuum. The residue was recrystallized from 1,2-dichloroethane to provide tan needles. This material was suspended in water; one equivalent of concentrated hydrochloric acid was added and the mixture was heated to dissolve the solids. The solution was treated with charcoal and then filtered. The filtrate was cooled and then made basic with sodium carbonate. The resulting precipitate was isolated by filtration, washed with water and then recrystallized from 1,2-dichloroethane to provide 2-ethylthiazolo[4,5-c]quinolin-4-amine as yellow needles, m.p. 169–171° C. Analysis: Calculated for $C_{12}H_{11}N_3S$: % C, 62.85; % H, 4.83; % N, 18.32; Found: % C, 62.79; % H, 4.86; % N, 18.22.

Example 10

2-Ethylthiazolo[4,5-c]quinolin-4-amine Hydrochloride

Concentrated hydrochloric acid (18.5 mmol) was added to a solution of 2-ethylthiazolo[4,5-c]quinolin-4-amine (4.25 g) in warm isopropanol. The reaction mixture was heated at reflux to reduce the volume and remove the water. The reaction mixture was cooled to ambient temperature. The precipitate was isolated by filtration and then dried to provide 2-ethylthiazolo[4,5-c]quinolin-4-amine hydrochloride as a solid, m.p. 268–270° C. Analysis: Calculated for $C_{12}H_{11}N_3S$ HCl: % C, 54.23; % H, 4.55; % N, 15.81; Found: % C, 54.25; % H, 4.63; % N, 15.71.

Example 11

2-Propylthiazolo[4,5-c]quinoline-5N-oxide

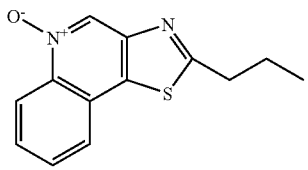

Part A

Using the general method of Example 7 Part A, 2-methylthiazolo[4,5-c]quinoline (2.50 g, 12.5 mmol) was reacted first with lithium diisopropylamide and then with ethyl iodide to provide 0.28 g of 2-propylthiazolo[4,5-c]quinoline as a yellow crystalline solid, m.p. 54° C. Analysis: Calculated for $C_{13}H_{12}N_2S$: % C, 68.39; % H, 5.30; % N, 12.27; Found: % C, 68.41; % H, 5.19; % N, 12.31.

Part B

Using the general method of Example 7 Part B, 2-propylthiazolo[4,5-c]quinoline (1.05 g, 4.6 mmol) was oxidized with 3-chloroperoxybenzoic acid to provide 0.65 g of 2-propylthiazolo[4,5-c]quinoline-5N-oxide as a yellow solid, m.p. 123° C. Analysis: Calculated for $C_{13}H_{12}N_2OS$: % C, 63.91; % H, 4.95; % N, 11.47; Found: % C, 63.53; % H, 4.88; % N, 11.44.

Example 12

2-Propylthiazolo[4,5-c]quinolin-4-amine

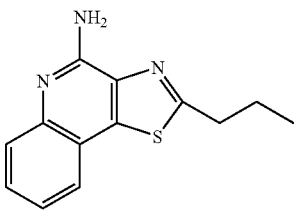

Using the general method of Example 8, 2-propylthiazolo[4,5-c]quinoline-5N-oxide (0.63 g) was reacted with trichloroacetyl isocyanate and the resulting amide intermediate was hydrolyzed using a solution of ammonia in methanol to provide 0.22 g of 2-propylthiazolo[4,5-c]quinolin-4-amine as a white crystalline solid, m.p. 140–142° C. Analysis: Calculated for $C_{13}H_{13}N_3S$: % C, 64.17; % H, 5.38; % N, 17.27; Found: % C, 64.31; % H, 5.39; % N, 17.13.

Example 13

2-Propylthiazolo[4,5-c]quinolin-4-amine Alternative Synthesis

Part A

Using the general method of Example 9 Part A, a suspension of 3-amino-quinoline-4-thiol (15 g) in butyric acid was reacted with butyric anhydride to provide 2-propylthiazolo[4,5-c]quinoline as a yellow oil.

Part B

Using the general method of Example 9 Part B, 2-propylthiazolo[4,5-c]quinoline (46 g) was oxidized with peracetic acid to provide 2-propylthiazolo[4,5-c]quinoline-5N-oxide as a yellow crystalline solid.

Part C

Ammonium hydroxide (50 mL) was added to a solution of 2-propylthiazolo[4,5-c]quinoline-5N-oxide (20 g) in chloroform (500 mL). The reaction mixture was cooled with an ice bath and then a solution of tosyl chloride (16 g) in chloroform was added dropwise. The reaction mixture was refluxed for 2 hours and then diluted with additional chloroform and water. The layers were separated. The organic layer was washed with aqueous sodium bicarbonate, dried over magnesium sulfate and then concentrated under vacuum. The residue was recrystallized from 1,2-dichloroethane to provide 2-propylthiazolo[4,5-c]quinolin-4-amine as a tan solid, m.p. 140–142° C. Analysis: Calculated for $C_{13}H_{13}N_3S$: % C, 64.17; % H, 5.38; % N, 17.27; Found: % C, 64.10; % H, 5.47; % N, 17.29.

Example 14

2-Propylthiazolo[4,5-c]quinolin-4-amine Hydrochloride

Using the general method of Example 10, 2-propylthiazolo[4,5-c]quinolin-4-amine (1.75 g) was reacted with 1 equivalent of concentrated hydrochloric acid to provide 2-propylthiazolo[4,5-c]quinolin-4-amine hydrochloride as an off-white crystalline solid, m.p. 234–237° C. Analysis: Calculated for $C_{13}H_{13}N_3S$ HCl: % C, 55.81; % H, 5.04; % N, 15.02; Found: % C, 55.86; % H, 5.02; % N, 14.99.

Example 15

2-Pentylthiazolo[4,5-c]quinoline-5N-oxide

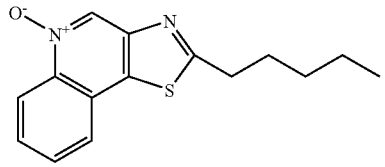

Part A

Using the general method of Example 7 Part A, 2-methylthiazolo[4,5-c]quinoline (2.0 g, 10 mmol) was reacted first with lithium diisopropylamide (5.5 mL of 2M in benzene) and then with 1-iodobutane (1.8 mL) to provide 1.1 g of 2-pentylthiazolo[4,5-c]quinoline as a yellow solid, m.p. 62–64° C.

Part B

Peracetic acid (1.50 mL of 32% in acetic acid) was added to a suspension of 2-pentylthiazolo[4,5-c]quinoline (1.25 g) in methyl acetate (50 mL). The reaction mixture was heated at reflux for 6 hours. The reaction mixture was allowed to cool to ambient temperature and then it was diluted with dichloromethane and washed first with sodium bicarbonate and then with water. The organic layer was dried over magnesium sulfate and then concentrated under vacuum to provide 1.20 g of a pale yellow solid. This material was recrystallized from ethyl acetate to provide 0.90 g of 2-pentylthiazolo[4,5-c]quinoline-5N-oxide as a white crystalline solid, m.p. 142–144° C. Analysis: Calculated for $C_{15}H_{16}N_2OS$: % C, 66.14; % H, 5.92; % N, 10.19; Found: % C, 65.63; % H, 5.83; % N, 10.28.

Example 16

2-Pentylthiazolo[4,5-c]quinolin-4-amine

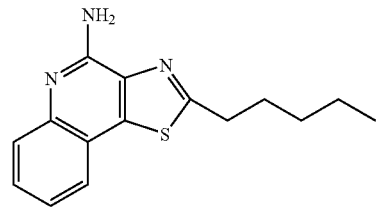

Trichloroacetyl isocyanate (0.51 mL) was added to a solution of 2-pentylthiazolo[4,5-c]quinoline-5N-oxide (0.78 g) in dichloromethane (50 mL). The reaction mixture was stirred at ambient temperature for about 75 minutes and then concentrated under vacuum to provide crude N-(2-pentylthiazolo[4,5-c]quinolin-4-yl)trichloroacetamide. The amide was combined with a solution of ammonia in methanol (40 mL of 2M). Dichloromethane was added to bring all of the material into solution. When the reaction was completed as indicated by thin layer chromatography, the reaction mixture was concentrated under vacuum. The residue was mixed with dichloromethane and sodium bicarbonate. The organic layer was separated, washed with sodium bicarbonate then with water, dried over magnesium sulfate and then concentrated under vacuum to provide a white solid. This material was recrystallized from ethyl acetate to provide 2-pentylthiazolo[4,5-c]quinolin-4-amine as an off-white crystalline solid, m.p. 119–121° C. Analysis: Calculated for $C_{15}H_{17}N_3S$: % C, 66.39; % H, 6.31; % N, 15.48; Found: % C, 66.21; % H, 6.35; % N, 15.39.

Example 17

2-Butylthiazolo[4,5-c]quinoline-5N-oxide

Part A

Using the general method of Example 7 Part A, 2-methylthiazolo[4,5-c]quinoline (2.50 g, 12.5 mmol) was reacted first with lithium diisopropylamide (7.0 mL of 2M in benzene) and then with 1-iodopropane (3.0 g) to provide 1.19 g of 2-butylthiazolo[4,5-c]quinoline as a yellow oil.

Part B

Using the general method of Example 15 Part B, 2-butylthiazolo[4,5-c]quinoline (1.33 g) was oxidized with peracetic acid to provide 0.5 g of 2-butylthiazolo[4,5-c]quinoline-5N-oxide as a solid, m.p. 133–135° C.

Example 18

2-Butylthiazolo[4,5-c]quinolin-4-amine

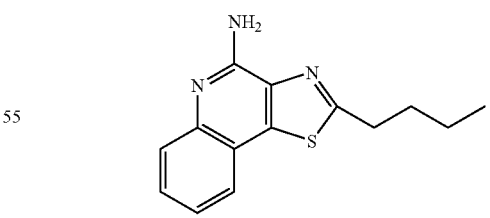

Using the general method of Example 16, 2-butylthiazolo[4,5-c]quinoline-5N-oxide (0.50 g) was converted to the amide and then hydrolyzed to provide 0.25 g of 2-butylthiazolo[4,5-c]quinolin-4-amine as a yellow crystalline solid, m.p. 149–151° C. Analysis: Calculated for $C_{14}H_{15}N_3S$: % C, 65.34; % H, 5.87; % N, 16.33; Found: % C, 64.88; % H, 5.84; % N, 16.03

Example 19

2-(1-Methyethyl)thiazolo[4,5-c]quinoline-5N-oxide

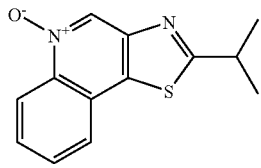

Part A

Using the general method of Example 7 Part A, 2-methylthiazolo[4,5-c]quinoline (1.50 g, 7.5 mmol) was reacted first with lithium diisopropylamide (15.0 mL of 2M in benzene) and then with methyl iodide (2.4 mL) to provide 0.97 g of 2-(1-methylethyl)lthiazolo[4,5-c]quinoline as a yellow oil.

Part B

Using the general method of Example 15 Part B, 2-(1-methylethyl)lthiazolo[4,5-c]quinoline (0.95 g) was oxidized with peracetic acid to provide 0.84 g of 2-(1-methylethyl)thiazolo[4,5-c]quinoline-5N-oxide as a yellow solid, m.p. 161–162° C.

Example 20

2-(1-Methyethyl)thiazolo[4,5-c]quinolin-4-amine

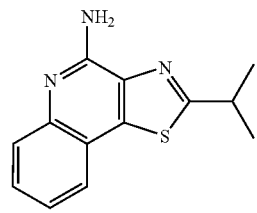

Using the general method of Example 16, 2-(1-methylethyl)thiazolo[4,5-c]quinoline-5N-oxide (0.84 g) was converted to the amide and then hydrolyzed to provide 0.16 g of 2-(1-methylethyl)thiazolo[4,5-c]quinolin-4-amine as yellow needles, m.p. 163–165° C. Analysis: Calculated for $C_{13}H_{13}N_3S$: % C, 64.17; % H, 5.38; % N, 17.27; Found: % C, 63.49; % H, 5.36; % N, 17.09

Example 21

2-(2-Phenyl-1-ethenyl)thiazolo[4,5-c]quinoline-5N-oxide

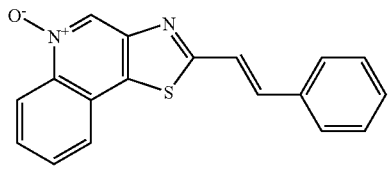

Part A

Using the general method of Example 7 Part A, 2-methylthiazolo[4,5-c]quinoline (5.0 g, 25 mmol) was reacted first with lithium diisopropylamide (15.0 mL of 2M in benzene) and then with benzaldehyde (3.8 mL) to provide 5.3 g 1-phenyl-2-thiazolo[4,5-c]quinolin-2-yl-1-ethanol as a solid, m.p. 147–148° C.

Part B

Concentrated hydrochloric acid was added dropwise to a suspension of 1-phenyl-2-thiazolo[4,5-c]quinolin-2-yl-1-ethanol (2.16 g) in water (40 mL) until all of the solid had dissolved. The reaction mixture was heated on a steam bath during the addition; heating was continued until analysis by thin layer chromatography indicated that all of the starting material had reacted. The reaction mixture was allowed to cool to ambient temperature and a precipitate formed. The reaction mixture was neutralized with sodium carbonate. Dichloromethane was added with stirring until all of the precipitate was in solution. The layers were separated and the aqueous layer was extracted with dichloromethane. The organic layers were combined, washed with water, dried over magnesium sulfate and then concentrated under vacuum to provide 2.2 g of a green solid. This material was recrystallized from ethyl acetate to provide 1.55 g of 2-(2-phenyl-1-ethenyl)thiazolo[4,5-c]quinoline as a green crystalline solid. Analysis: Calculated for: $C_{18}H_{12}N_2S$: % C, 74.97; % H, 4.19; % N, 9.71; Found: % C, 74.89; % H, 4.17; % N, 9.72.

Part C

Peracetic acid (1.32 mL of 32% in acetic acid) was added to a suspension of 2-(2-phenyl-1-ethenyl)thiazolo[4,5-c]quinoline (1.20 g) in methyl acetate (50 mL). A precipitate formed. Ethanol was added to the reaction mixture until all of the precipitate was dissolved. The reaction mixture was heated at reflux overnight and then cooled to ambient temperature. The resulting precipitate was isolated by filtration, dried and then recrystallized from methanol/dichloromethane to provide 2-(2-phenyl-1-ethenyl)thiazolo[4,5-c]quinoline-5N-oxide as a yellow solid, m.p. 268–270° C. Analysis: Calculated for: $C_{18}H_{12}N_2OS$: % C, 71.03; % H, 3.97; % N, 9.20; Found: % C, 69.94; % H, 3.87; % N, 9.05.

Example 22

2-(2-Phenyl-1-ethenyl)thiazolo[4,5-c]quinolin-4-amine

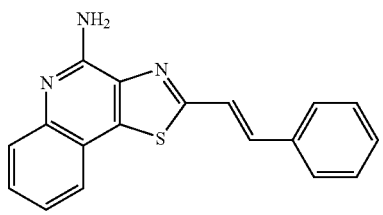

Using the general method of Example 16, 2-(2-phenyl-1-ethenyl)thiazolo[4,5-c]quinoline-5N-oxide (0.67 g) was converted to the trichloroacetamide then hydrolyzed to provide 0.43 g of 2-(2-phenyl-1-ethenyl)thiazolo[4,5-c]quinolin-4-amine as a yellow crystalline solid, m.p. 239–241° C. Analysis: Calculated for $C_{18}H_{13}N_3S$: % C, 71.26; % H, 4.32; % N, 13.85; Found: % C, 70.73; % H, 4.15; % N, 13.68.

Example 23

2-(2-Phenyl-1-ethyl)thiazolo[4,5-c]quinoline-5N-oxide

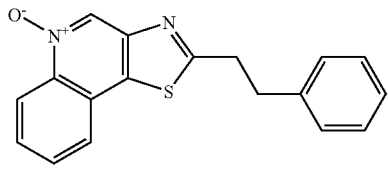

Part A

A small amount of catalyst (5% palladium on activated carbon) was added to a suspension of 2-(2-phenyl-1-ethenyl)thiazolo[4,5-c]quinoline (1.16 g, Example 21 Part B) in acetic acid (200 mL). The mixture was reduced on a Parr apparatus under a 50 psi (3.5 Kg/cm$^2$) hydrogen atmosphere for 1 day. The reaction mixture was filtered to remove the catalyst. The filtrate was concentrated under vacuum. The residue was dissolved in dichloromethane, washed with sodium bicarbonate then with water, dried over magnesium sulfate and then concentrated under vacuum to provide 0.88 g of 2-(2-phenyl-1-ethyl)thiazolo[4,5-c]quinoline as an oily solid.

Part B

Using the general method of Example 15 Part B, 2-phenylethylthiazolo[4,5-c]quinoline (0.90 g) was oxidized with peracetic acid to provide 0.63 g of 2-(2-phenyl-1-ethyl)thiazolo[4,5-c]quinoline-5N-oxide as an orange crystalline solid, m.p. 165–169° C. Analysis: Calculated for $C_{18}H_{14}N_2OS$: % C, 70.56; % H, 4.60; % N, 9.14; Found: % C, 69.59; % H, 4.50; % N, 9.04.

Example 24

2-(2-Phenyl-1-ethyl)thiazolo[4,5-c]quinolin-4-amine

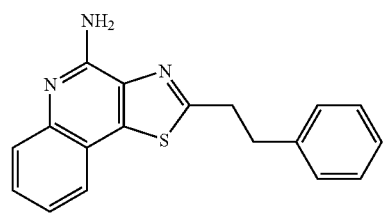

Using the general method of Example 16, 2-(2-phenyl-1-ethyl)thiazolo[4,5-c]quinoline-5N-oxide (0.63 g) was converted to the trichloroacetamide then hydrolyzed to provide 0.21 g of 2-(2-phenyl-1-ethyl)thiazolo[4,5-c]quinolin-4-amine as a yellow crystalline solid, m.p. 158–159° C. Analysis: Calculated for $C_{18}H_{15}N_3S$: % C, 70.79; % H, 4.95; % N, 13.75; Found: % C, 70.29; % H, 4.90; % N, 13.66.

Example 25

2-Methyl-1-(thiazolo[4,5-c]quinolin-2-yl)-2-propanol-5N-oxide

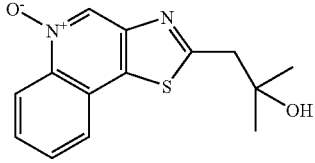

Part A

Under an argon atmosphere, anhydrous tetrahydrofuran (150 mL) was added to a dried flask containing 2-methylthiazolo[4,5-c]quinoline (8.40 g). The reaction mixture was cooled to −78° C. with a dry ice bath. Lithium diisopropylamide (23 mL of 2.0 M in benzene) was added dropwise. After about 50 minutes, acetone (5 mL) was added and the reaction mixture was allowed to warm to 0° C. After several hours the reaction was quenched with water, diluted with chloroform and then washed with water. The organic layer was dried over magnesium sulfate and then concentrated under vacuum. The residue was suspended in water (200 mL) and the mixture was heated. Hydrochloric acid (6N) was slowly added until all of the solid dissolved. Charcoal was added and the mixture was heated with stirring for about 5 minutes. The mixture was filtered to remove the charcoal. The filtrate was neutralized with sodium carbonate and then extracted with chloroform. The chloroform extract was washed several times with water, dried over magnesium sulfate and then concentrated under vacuum to provide 8.0 g of a light brown solid. This material was recrystallized from dichloromethane/hexanes to provide 5.0 g of 2-methyl-1-(thiazolo[4,5-c]quinolin-2-yl)-2-propanol as a yellow crystalline solid, m.p. 155–157° C. Analysis: Calculated for $C_{14}H_{14}N_2OS$: % C, 65.08; % H, 5.46; % N, 10.84; Found: % C, 64.97; % H, 5.33; % N, 10.90.

Part B

Peracetic acid (4.8 mL of 32% in acetic acid) was added to a suspension of 2-methyl-1-(thiazolo[4,5-c]quinolin-2-yl)-2-propanol (3.0 g) in methyl acetate (200 mL). The reaction mixture was heated at reflux overnight, cooled to ambient temperature and then concentrated under vacuum. The residue was dissolved in dichloromethane and then combined with sodium bicarbonate and stirred vigorously. The resulting precipitate was isolated by filtration and then dissolved in methanol/dichloromethane. This solution was concentrated under vacuum. The residue was combined with dichloromethane and then filtered to remove undissolved material. The filtrate was concentrated under vacuum to provide 2.6 g of the desired N-oxide. A small portion (0.2 g) was recrystallized from methanol/water to provide 2-methyl-1-(thiazolo[4,5-c]quinolin-2-yl)-2-propanol-5N-oxide as a solid, m.p. 187–189° C. Analysis: Calculated for $C_{14}H_{14}N_2O_2S$ ⅓$H_2O$: % C, 59.98; % H, 5.27; % N, 9.99; Found: % C, 60.09; % H, 5.03; % N, 10.00.

Example 26

2-(4-Aminothiazolo[4,5-c]quinolin-2-yl)-1,1-dimethylethyl Carbamate

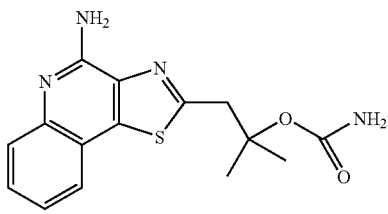

Trichloroacetyl isocyanate (3.2 mL0 was added to a solution of 2-methyl-1-(thiazolo[4,5-c]quinolin-2-yl)-2-propanol-5N-oxide (2.4 g) in dichloromethane (250 mL). The reaction mixture was stirred at ambient temperature for 1 hour and then concentrated under vacuum. The residue was stirred with a solution of ammonia in methanol (150 mL of 2M) for 2 hours. The methanol was removed under vacuum. The residue was suspended in a mixture of dichloromethane and ethyl acetate and then washed with sodium bicarbonate. The undissolved material was isolated by filtration, washed with water, washed with dichloromethane and then recrystallized from methanol/dichloromethane to provide 1.6 g of 2-(4-aminothiazolo[4,5-c]quinolin-2-yl)-1,1-dimethylethyl carbamate as a solid, m.p. 222–223° C. Analysis: Calculated for $C_{15}H_{16}N_4O_2S$: % C, 56.94; % H, 5.09; % N, 17.70; Found: % C, 56.71; % H, 5.08; % N, 17.52.

Example 27

2-(Ethoxymethyl)thiazolo[4,5-c]quinoline-5N-oxide

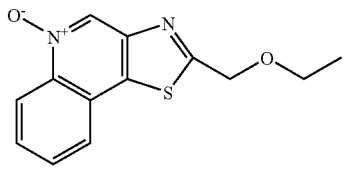

Part A

Ethoxyacetyl chloride (6 mL, 53.8 mmol) was added to a suspension of 3-aminoquinoline-4-thiol (4.6 g, 26.1 mmol) in ethoxyacetic acid (50 mL). The reaction mixture was heated at 60° C. overnight. The reaction mixture was concentrated under vacuum to remove a portion of the ethoxyacetic acid. The residue was combined with water (100 mL) and a precipitate formed. The mixture was made basic with 50% sodium hydroxide. The precipitate was isolated by filtration, washed with water and then dried to provide 2-(ethoxymethyl)thiazolo[4,5-c]quinoline as a fluffy green solid.

Part B

Peracetic acid (1.0 mL of 32% in acetic acid) was added to a solution of 2-(ethoxymethyl)thiazolo[4,5-c]quinoline (1.0 g) in ethanol. The reaction mixture was stirred at ambient temperature for 1 week. The reaction mixture was concentrated under vacuum and then azeotroped with heptane to remove acetic acid. The residue was dissolved in dichloromethane, washed with sodium bicarbonate, washed with water, dried over magnesium sulfate and then concentrated under vacuum. The residue was recrystallized from isopropanol to provide 2-(ethoxymethyl)thiazolo[4,5-c] quinoline-5N-oxide as a yellow crystalline solid, m.p. 138–140° C. Analysis: Calculated for $C_{13}H_{12}N_2O_2S$: % C, 59.98; % H, 4.65; % N, 10.76; Found: % C, 59.85; % H, 4.66; % N, 10.71.

Example 28

2-(Ethoxymethyl)thiazolo[4,5-c]quinoline-4-amine

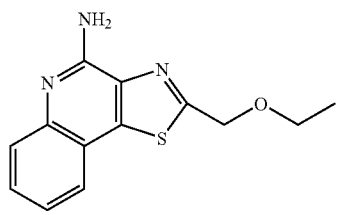

Trichloroacetyl isocyanate (0.7 mL) was added to a solution of 2-(ethoxymethyl)thiazolo[4,5-c]quinoline-5N-oxide (1.0 g) in dichloromethane (50 mL). The reaction mixture was stirred at ambient temperature for 2 hours and then concentrated under vacuum to provide N-(2-(ethoxymethyl)thiazolo[4,5-c]quinolin-4-yl)trichloroacetamide. The amide was taken up in methanol and then combined with 1 equivalent of sodium methoxide. The reaction mixture was stirred at ambient temperature for 30 minutes and then concentrated under vacuum. The reaction was run a second time using 2 g of the N-oxide. The products were combined and recrystallized from isopropanol to provide 2.25 g of 2-(ethoxymethyl)thiazolo[4,5-c]quinoline-4-amine as light yellow needles, m.p. 149–151° C. Analysis: Calculated for $C_{13}H_{13}N_3OS$: % C, 60.21; % H, 5.05; % N, 16.20; Found: % C, 59.86; % H, 4.97; % N, 16.16.

Example 29

2-(Methoxymethyl)thiazolo[4,5-c]quinoline-5N-oxide

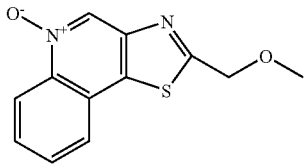

Part A

Methoxyacetyl chloride (1.8 mL) was added to a mixture of 3-aminoquinoline-4-thiol (2.8 g) in methoxyacetic acid (15 mL). The reaction was heated at about 140° C. for 1 hour and then allowed to cool to ambient temperature. The reaction mixture was diluted with a small amount of water, made basic with 10% sodium hydroxide and then extracted with dichloromethane (300 mL). The extract was washed with sodium bicarbonate, washed with water, dried over magnesium sulfate and then concentrated under vacuum to provide crude product as a dark oil. The oil was dissolved in dichloromethane and then placed on a layer of silica gel. The silica gel was eluted with 1:1 hexane:ethyl acetate. The eluant was concentrated under vacuum to provide 2.3 g of 2-(methoxymethyl)thiazolo[4,5-c]quinoline as an orange solid.

Part B

Using the general method of Example 27 Part B, 2-(methoxymethyl)thiazolo[4,5-c]quinoline (1.7 g) was oxidized to provide 1.8 g of 2-(methoxymethyl)thiazolo[4,5-c]quinoline-5N-oxide as yellow needles, m.p. 151–153° C. Analysis: Calculated for $C_{12}H_{10}N_2OS$: % C, 58.52; % H, 4.09; % N, 11.37; Found: % C, 57.95; % H, 3.98; % N, 11.3.

Example 30

2-(Methoxymethyl)thiazolo[4,5-c]quinolin-4-amine

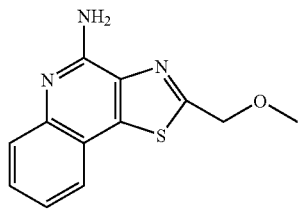

Using the general method of Example 28, 2-(methoxymethyl)thiazolo[4,5-c]quinoline-5N-oxide (1.3 g) was reacted to form the trichloroacetamide and then hydrolyzed to provide 2-(methoxymethyl)thiazolo[4,5-c]quinolin-4-amine as light yellow needles, m.p. 183–185° C. Analysis: Calculated for $C_{12}H_{11}N_3OS$: % C, 58.76; % H, 4.52; % N, 17.13; Found: % C, 58.69; % H, 4.34; % N, 17.14.

Example 31

2-(2-Methylpropyl)thiazolo[4,5-c]quinoline-5N-oxide

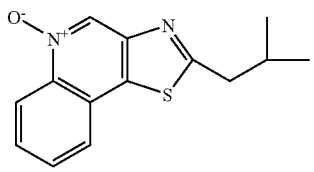

Part A

3-Aminoquinoline-4-thiol (4.6 g) was added to polyphosphoric acid (80 g). Isovaleric acid (3.5 mL) was added and the reaction mixture was heated at 140° C. for 2 hours. The reaction mixture was poured into a mixture of ice and water (300 mL). The mixture was filtered through a layer of Celite® filter aid to remove some insoluble material. The filtrate was made alkaline with 50% sodium hydroxide while cooling with ice and then extracted with chloroform. The extract was washed with water, dried over magnesium sulfate and then concentrated under vacuum to provide an oil. The oil was dissolved in dichloromethane and then placed on a layer of silica gel and eluted with 1:1 ethyl acetate:hexanes. The eluant was concentrated under vacuum to provide 2-(2-methylpropyl)thiazolo[4,5-c]quinoline.

Part B

Using the general method of Example 27 Part B, 2-(2-methylpropyl)thiazolo[4,5-c]quinoline (5.2 g) was oxidized to provide 2.5 g of 2-(2-methylpropyl)thiazolo[4,5-c]quinoline-5N-oxide as a yellow solid.

Example 32

2-(2-Methylpropyl)thiazolo[4,5-c]quinolin-4-amine

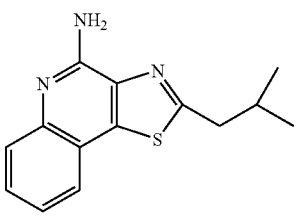

Using the general method of Example 28, 2-(2-methylpropyl)thiazolo[4,5-c]quinoline-5N-oxide (2.5 g) was reacted to form the trichloroacetamide and then hydrolyzed to provide 2-(2-methylpropyl)thiazolo[4,5-c]quinolin-4-amine as light yellow platelets, m.p. 123–125° C. Analysis: Calculated for $C_{14}H_{15}N_3S$: % C, 65.34; % H, 5.87; % N, 16.33; Found: % C, 64.87; % H, 5.79; % N, 16.18.

Example 33

2-Benzylthiazolo[4,5-c]quinoline-5N-oxide

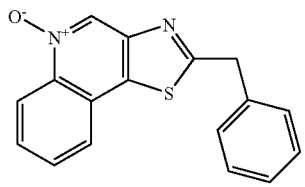

Part A

Thionyl chloride (1.5 g) was added dropwise to a cooled solution of phenyl acetic acid (2 g) in dichloromethane (10 mL). This mixture was allowed to stir at ambient temperature for 1 hour to provide a solution containing phenylacetyl chloride. Triethyl amine (4.3 mL) was added to a suspension of 3-aminoquinolin-4-ol in dichloromethane (10 mL) and the resulting mixture was cooled in an ice bath. The phenylacetyl chloride solution was added dropwise to the cooled mixture. The reaction mixture was allowed to stir at ambient temperature overnight. The resulting thick oily precipitate was diluted with water (10 mL) and then stirred rapidly for 1 hour. The reaction mixture was filtered. Thin layer chromatography showed that both the isolated solid and the filtrate contained the desired product. The filtrate was diluted with dichloromethane and water. The dichloromethane layer was separated, dried over magnesium sulfate and then concentrated under vacuum. The residue was combined with the previously isolated solid and recrystallized from 80:20 isopropanol:water to provide 1.3 g of N-(4-hydroxyquinolin-3-yl)phenylacetamide as needles, m.p. 253–255° C. Analysis: Calculated for: $C_{17}H_{14}N_2O_2$: % C, 73.37; % H, 5.07; % N, 10.07; Found: % C, 73.16; % H, 5.03; % N, 10.07.

Part B

Phosphorous pentasulfide (1.6 g) was added to a suspension of N-(4-hydroxyquinolin-3-yl)phenylacetamide (1.0 g) in pyridine. The reaction mixture was heated at reflux until the reaction was complete. The reaction mixture was concentrated under vacuum and then azeotroped with water to remove most of the pyridine. The residue was combined with water, neutralized with sodium carbonate and then extracted with dichloromethane. The extract was washed with water, dried over magnesium sulfate and then concentrated under vacuum to provide 2-benzylthiazolo[4,5-c]quinoline as a solid.

Part C

Using the general method of Example 27 Part B, 2-benzylthiazolo[4,5-c]quinoline (3.3 g) was oxidized to provide 2.1 g of 2-benzylthiazolo[4,5-c]quinoline-5N-oxide as a yellow solid, m.p. 185–186° C. Analysis: Calculated for $C_{17}H_{12}N_2OS$: % C, 69.84; % H, 4.14; % N, 9.58; Found: % C, 69.51; % H, 4.06; % N, 9.55

Example 34

2-Benzylthiazolo[4,5-c]quinolin-4-amine Hydrochloride

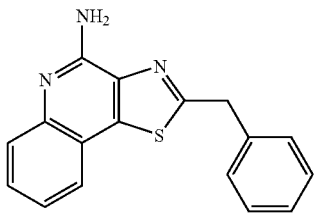

Trichloroacetyl isocyanate (1.2 mL, 10.3 mmol) was added to a solution of 2-benzylthiazolo[4,5-c]quinoline-5N-oxide (2.0 g, 6.8 mmol) in dichloromethane (100 mL). The reaction mixture was stirred at ambient temperature for 2 hours and then concentrated to provide crude N-(2-benzylthiazolo[4,5-c]quinolin-4-yl)trichloroacetamide. The amide was dissolved in methanol. Sodium methoxide (1 equivalent) was added. The reaction mixture was heated on a steam bath for 30 minutes and then allowed to cool to ambient temperature. The resulting precipitate was isolated by filtration and then suspended in a mixture of methanol and isopropanol. Hydrochloric acid (1 equivalent) was added and all of the solid dissolved initially. A white solid crystallized out. This material was isolated by filtration, washed with isopropanol and then dried to provide 1.5 g of 2-benzylthiazolo[4,5-c]quinolin-4-amine hydrochloride, m.p. 152–155° C. Analysis: Calculated for: $C_{17}H_{13}N_3S\cdot HCl$: % C, 62.28; % H, 4.30; % N, 12.82; Found: % C, 62.05; % H, 4.23; % N, 12.82.

Example 35

8-Methyl-2-propylthiazolo[4,5-c]quinoline-5N-oxide

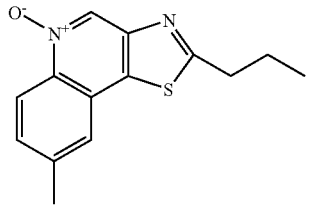

Part A

Catalyst (0.10 g of 10% platinum on carbon) was added to a solution of 6-methyl-3-nitroquinolin-4-ol (1 g) in ethanol (25 mL) and ammonium hydroxide (0.5 mL). The mixture was reduced on a Parr apparatus at ambient temperature under a hydrogen atmosphere. The reaction mixture was filtered to remove the catalyst and then concentrated under vacuum. The residue was combined with water and heated. Hydrochloric acid was added dropwise until all of the solid had dissolved. Activated carbon was added to the solution. The mixture was filtered. Hydrochloric acid (2 mL of 12N) was added to the filtrate. This recrystallization was run three times to provide 0.50 g of 3-amino-6-methylquinolin-4-ol hydrochloride, m.p. >310° C. Analysis: Calculated for $C_{10}H_{10}N_2O\cdot HCl$: % C, 57.02; % H, 5.26; % N, 13.30; Found: % C, 56.92; % H, 5.16; % N, 13.24.

Part B

Triethylamine (11.46 mL) was added to a suspension of 3-amino-6-methylquinolin-4-ol hydrochloride in dichloromethane (400 mL). Butyryl chloride (4.46 mL) was added. The reaction mixture was heated on a steam bath for 30 minutes. The solution was diluted with sodium bicarbonate and then filtered. The filtrate was washed with bicarbonate and then concentrated under vacuum. The residue was recrystallized from isopropanol to provide 3-butyramido-6-methylquinolin-4-ol hemihydrate as a solid, m.p. 274–277° C. Analysis: Calculated for $C_{14}H_{16}N_2O_2\cdot\frac{1}{2}H_2O$: % C, 66.39; % H, 6.76; % N, 11.06; Found: % C, 66.56; % H, 6.46; % N, 11.03.

Part C

Phosphorous pentasulfide (12.9 g) was added to a mixture of 3-butyramido-6-methylquinolin-4-ol hemihydrate (7.12 g) in pyridine. The reaction mixture was heated at reflux for 90 minutes, combined with a mixture of ice and sodium carbonate and then extracted with dichloromethane. The extract was concentrated under vacuum. The residue was diluted with toluene and then concentrated under vacuum to provide a crude solid. This material was purified using column chromatography eluting with 20% dichloromethane in ethyl acetate to provide 8-methyl-2-propylthiazolo[4,5-c]quinoline as a yellow solid.

Part D

Using the general method of Example 7 Part B, 8-methyl-2-propylthiazolo[4,5-c]quinoline (4.0 g) was oxidized using 3-chloroperoxybenzoic acid to provide 4.19 g of crude product which was recrystallized from isopropanol to provide 2.0 g of 8-methyl-2-propylthiazolo[4,5-c]quinoline-5N-oxide as a solid, m.p. 143–145° C. Analysis: Calculated for $C_{14}H_{14}N_2OS$: % C, 65.09; % H, 5.46; % N, 10.84; Found: % C, 64.86; % H, 5.40; % N, 10.88.

Example 36

8-Methyl-2-propylthiazolo[4,5-c]quinolin-4-amine

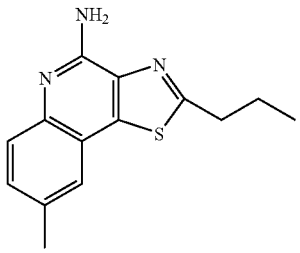

Using the general method of Example 28, 8-methyl-2-propylthiazolo[4,5-c]quinoline-5N-oxide was converted to N-(8-methyl-2-propylthiazolo[4,5-c]quinolin-4-yl)trichloroacetamide and then hydrolyzed to provide 1.32 g of 8-methyl-2-propylthiazolo[4,5-c]quinolin-4-amine as a crystalline solid, m.p. 147–149° C. Analysis: Calculated for $C_{14}H_{15}N_3S$: % C, 63.54; % H, 5.87; % N, 16.33; Found: % C, 64.97; % H, 5.76; % N, 16.25.

Example 37

(4-Aminothiazolo[4,5-c]quinolin-2-yl)-methanol

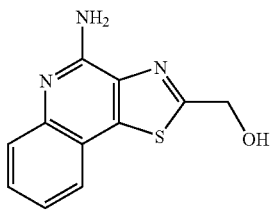

Part A

Triethylamine (7.3 mL) was added to a suspension of 3-aminoquinolin-4-ol (5 g) in dichloromethane (50 mL). The mixture was cooled in an ice bath and then acetoxyacetyl chloride (3 mL) was added dropwise. The reaction mixture was stirred at ambient temperature for 2 hours. The resulting thick precipitate was diluted with water (10 mL), stirred rapidly for 20 minutes and then isolated by filtration. Thin layer chromatography indicated that both the solid and the filtrate contained the desired product. The filtrate was concentrated under vacuum. The residue was mixed with water and then filtered. The combined solids were recrystallized from 80:20 isopropanol:water to provide N-(4-hydroxyquinolin-3-yl)acetoxyacetamide, m.p. 224–225° C.

Part B

Using the general method of Example 33 Part B, N-(4-hydroxyquinolin-3-yl)acetoxyacetamide (5.3 g) was reacted with phosphorous pentasulfide to provide 2.9 g of thiazolo[4,5-c]quinolin-2-ylmethyl acetate as a solid.

Part C

Using the general method of Example 27 Part B, thiazolo[4,5-c]quinolin-2-ylmethyl acetate (2.8 g) was oxidized with peracetic acid to provide thiazolo[4,5-c]quinolin-2-ylmethyl acetate-5N-oxide as a tan crystalline solid.

Part D

Trichloroacetyl isocyanate (0.65 mL) was added to a solution of thiazolo[4,5-c]quinolin-2-ylmethyl acetate-5N-oxide (1.0 g) in dichloromethane (50 mL). The reaction was stirred at ambient temperature for 2 hours and then concentrated under vacuum. The residue was dissolved in methanol. Sodium methoxide (1 equivalent) was added and the reaction mixture was stirred at ambient temperature overnight. The resulting precipitate was isolated by filtration and dried to provide 0.68 g of (4-aminothiazolo[4,5-c]quinolin-2-yl)methanol as a white solid, m.p. 247–249° C. Analysis: Calculated for $C_{11}H_9N_3OS$: % C, 57.13; % H, 3.92; % N, 18.17; Found: % C, 56.85; % H, 3.96; % N, 17.83.

Example 38

2-Methyloxazolo[4,5-c]quinolin-4-amine

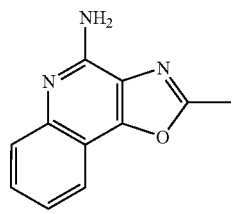

Part A

3-Aminoquinolin-4-ol (6 g) was refluxed with acetic anhydride (8 eq.) until analysis by thin layer chromatography indicated that the reaction was complete. The reaction mixture was cooled, diluted with ice and water, made basic with 10% sodium hydroxide and then extracted with dichloromethane. The extract was washed with water and brine, dried over magnesium sulfate and then concentrated under vacuum. The residue was purified by column chromatography (silica gel eluting with methanol/ethyl acetate) to provide 5.1 g of 2-methyloxazolo[4,5-c]quinoline.

Part B

A mixture of 2-methyloxazolo[4,5-c]quinoline (5.0 g), peracetic acid (5 eq.) and ethanol was stirred at ambient temperature. After 2 hours more peracetic acid (2 eq) was added and stirring was continued for 3 additional hours. The reaction mixture was concentrated under vacuum. The residue was azeotroped with heptane to provide 4.2 g of 2-methyloxazolo[4,5-c]quinoline-5N-oxide.

Part C

Trichloroacetyl isocyanate (3.6 mL) was slowly added to a cooled mixture of 2-methyloxazolo[4,5-c]quinoline-5N-oxide (4.0 g) and dichloromethane. The reaction mixture was stirred for several hours and then concentrated under vacuum to provide crude N-(2-methyloxazolo[4,5-c]quinolin-4-yl)trichloroacetamide. This material was combined with a solution of ammonia in methanol (2M) and stirred for 1 hour. The reaction mixture was concentrated under vacuum, diluted with water and then extracted with dichloromethane. The extract was washed with water and brine, dried over magnesium sulfate and then concentrated under vacuum. The residue was purified by column chromatography (silica gel eluting with ethyl acetate/hexane) to provide 1.2 g of 2-methyloxazolo[4,5-c]quinolin-4-amine as a solid, m.p. 195–197° C. Analysis: Calculated for $C_{11}H_9N_3O$: % C, 66.32; % H, 4.55; % N, 21.09; Found: % C, 65.96; % H, 4.44; % N, 20.68.

Example 39

2-Ethyloxazolo[4,5-c]quinolin-4-amine

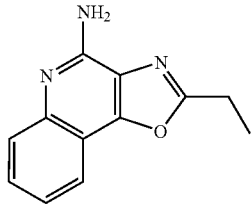

Part A

3-Aminoquinolin-4-ol hydrochloride (6 g) was refluxed with propanoic anhydride (8 eq.) until analysis by thin layer chromatography indicated that the reaction was complete. The reaction mixture was cooled, diluted with ice and water, made basic with 10% sodium hydroxide and then extracted with dichloromethane. The extract was washed with water and brine, dried over magnesium sulfate and then concentrated under vacuum. The residue was purified by column chromatography (silica gel eluting with methanol/ethyl acetate) to provide 4.0 g of 2-ethyloxazolo[4,5-c]quinoline.

Part B

2-Ethyloxazolo[4,5-c]quinoline (3.5 g), peracetic acid (4.5 mL of 32% in acetic acid) and methyl acetate (40 mL) were combined and heated at 50° C. for several hours. The reaction mixture was concentrated under vacuum. The residue was slurried with hexane and then filtered to provide 2.5 g of 2-ethyloxazolo[4,5-c]quinoline-5N-oxide as a solid.

Part C

Trichloroacetyl isocyanate (2 mL) was slowly added to a cooled mixture of 2-ethyloxazolo[4,5-c]quinoline-5N-oxide (2.5 g) and dichloromethane. The reaction mixture was stirred for several hours and then concentrated under vacuum to provide crude N-(2-ethyloxazolo[4,5-c]quinolin-4-yl)trichloroacetamide. This material was combined with a solution of ammonia in methanol (2M) and stirred for 1 hour. The reaction mixture was concentrated under vacuum, diluted with water and then extracted with dichloromethane. The extract was washed with water and brine, dried over magnesium sulfate and then concentrated under vacuum. The residue was purified by column chromatography (silica gel eluting with ethyl acetate/hexane) to provide 2-ethyloxazolo[4,5-c]quinolin-4-amine as a solid, m.p. 175–178° C. Analysis: Calculated for $C_{12}H_{11}N_3O$: % C, 67.59; % H, 5.20; % N, 19.71; Found: % C, 67.19; % H, 4.86; % N, 20.43.

Example 40

2-Butyloxazolo[4,5-c]quinoline-5N-oxide

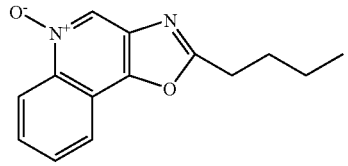

Part A

3-Aminoquinolin-4-ol hydrochloride (1.97 g, 10.0 mmol), triethylamine (1.01 g, 10.1 mmol) and valeric anhydride (9.3 g, 50.0 mmol) were combined and then heated at reflux for 18 hours. The reaction mixture was cooled to ambient temperature and then poured over ice. The mixture was adjusted to pH 12 with 10% sodium hydroxide. The mixture was stirred until all of the ice melted and then it was extracted with diethyl ether. The ether extracts were combined, dried over magnesium sulfate and then concentrated under vacuum to provide a tan solid. This material was purified by flash chromatography eluting with 3:2 ethyl acetate:dichloromethane to provide 1.45 g of 2-butyloxazolo[4,5-c]quinoline.

Part B

Peracetic acid (1.6 g, 6.8 mmol of 32% in acetic acid) was added with stirring to a solution of 2-butyloxazolo[4,5-c]quinoline (1.4 g, 6.2 mmol) in ethanol (50 mL). The reaction mixture was stirred at ambient temperature for 3 days and then quenched with saturated potassium carbonate solution. The layers were separated. The organic layer was concentrated under vacuum to provide a tan solid. This material was slurried with diethyl ether and then filtered to provide 0.6 g of 2-butyloxazolo[4,5-c]quinolin-5N-oxide, m.p. 120–121° C. Analysis: Calculated for $C_{14}H_{14}N_2O_2$: % C, 69.41; % H, 5.82; % N, 11.56; Found: % C, 69.22; % H, 5.76; % N, 11.59.

Example 41

2-Butyloxazolo[4,5-c]quinolin-4-amine

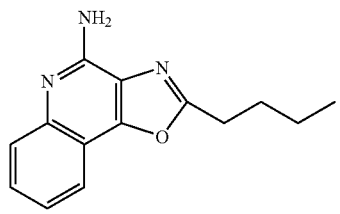

Under a nitrogen atmosphere, trichloroacetyl isocyanate (0.6 g, 3.40 mmol) was added with stirring to a solution of 2-butyloxazolo[4,5-c]quinolin-5N-oxide (0.55 g, 2.27 mmol) in anhydrous dichloromethane (20 mL). The reaction mixture was maintained at ambient temperature for 2 hours and then concentrated under vacuum to provide crude N-(2-butyloxazolo[4,5-c]quinolin-4-yl)trichloroacetamide as an oil. The oil was taken up in methanol (25 mL). Sodium methoxide (0.49 g of 25%, 2.27 mmol) was added to the solution. The reaction mixture was heated at reflux for 2 hours and then concentrated under vacuum. The residue was taken up in ethyl acetate and washed with water. The ethyl acetate layer was concentrated under vacuum to provide an orange solid. This material was purified twice using flash chromatography eluting with ethyl acetate the first time and with 30% dichloromethane in ethyl acetate the second time to provide 0.15 g of 2-butyloxazolo[4,5-c]quinolin-4-amine, m.p. 96–98° C. Analysis: Calculated for $C_{14}H_{15}N_3O$: % C, 69.69; % H, 6.27; % N, 17.41; Found: % C, 69.23; % H, 6.06; % N, 17.07.

Example 42

2-Propylthiazolo[4,5-c]quinolin-4,8-diamine

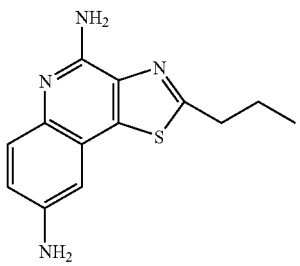

Part A

Potassium nitrate (0.46 g, 4.52 mmol) was added to a solution of 2-propylthiazolo[4,5-c]quinolin-4-amine (1 g, 4.11 mmol, Example 12) in sulfuric acid (10 mL). The reaction mixture was stirred at ambient temperature for 30 minutes, then poured onto ice, neutralized (pH=7) with ammonium hydroxide (150 mL) and then extracted with dichloromethane. The extract was washed with sodium bicarbonate, dried over magnesium sulfate and then concentrated under vacuum to provide 1 g of a yellow solid. This material was recrystallized from isopropanol/water to provide 0.84 g of 8-nitro-2-propylthiazolo[4,5-c]quinoline as a yellow solid, m.p. 228–230° C. Analysis: Calculated for $C_{13}H_{12}N_4O_2S$: % C, 54.15; % H, 4.20; % N, 19.43; Found: % C, 54.22; % H, 4.05; % N, 19.04.

Part B

Catalyst (0.13 g of palladium on carbon) was added to a solution of 8-nitro-2-propylthiazolo[4,5-c]quinoline (1.31 g) in ethanol. The mixture was reduced on a Parr apparatus under a hydrogen atmosphere. The reaction mixture was filtered to remove catalyst and the filter cake was washed with additional ethanol. The filtrate was concentrated under vacuum at 50° C. and then oven dried under nitrogen to provide 2-propylthiazolo[4,5-c]quinolin-4,8-diamine as a yellow crystalline solid, m.p. 190–192° C., Analysis: Calculated for $C_{13}H_{14}N_4S$: % C, 60.44; % H, 5.46; % N, 21.69; Found: % C, 60.11; % H, 5.45; % N, 21.96.

Example 43

2-Propyloxazolo[4,5-c]quinolin-4-amine

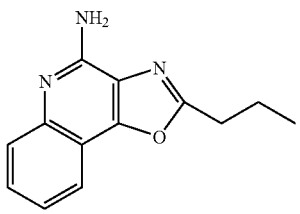

Part A

A mixture of 3-aminoquinolin-4-ol hydrochloride (1.97 g, 10.0 mmol), butyric anhydride (3.15 g, 20 mmol) and pyridine (25 mL) was heated at reflux overnight. The reaction mixture was cooled and then poured over ice. The mixture was made basic (pH 11) with 1 N sodium hydroxide and then it was extracted with diethyl ether (3×100 mL). A precipitate was removed by filtration. The ether extracts were combined, dried over magnesium sulfate and then concentrated to provide 1.1 g of 2-propyloxazolo[4,5-c]quinoline as an off white solid.

Part B

3-Chloroperoxybenzoic acid (1.0 eq. of 60%) was added with stirring to a solution of 2-propyloxazolo[4,5-c]quinoline (1.0 g, 4.7 mmol) in chloroform (30 mL). The reaction mixture was stirred at ambient temperature overnight and then quenched with a saturated potassium carbonate solution. The layers were separated. The aqueous layer was extracted with dichloromethane. The organic layers were combined and concentrated. The resulting crude product was purified by flash chromatography eluting with 8:2 ethyl acetate:dichloromethane to provide 1.0 g of 2-propyloxazolo[4,5-c]quinoline-5N-oxide as a tan solid.

Part C

Trichloroacetyl isocyanate (0.9 g, 5.25 mmol) was added with stirring to a solution of 2-propyloxazolo[4,5-c]quinoline-5N-oxide (0.8 g, 3.5 mmol) in dichloromethane (30 mL). The reaction mixture was stirred at ambient temperature for 2.5 hours and then concentrated under vacuum to provide crude N-(2-propyloxazolo[4,5-c]quinolin-4-yl)trichloroacetamide. The amide was dissolved in methanol (50 mL) and then combined with sodium methoxide (1.0 eq of 25% in methanol) and heated at reflux for 2 hours. The reaction mixture was concentrated under vacuum. The residue was taken up in diethyl ether and water. The ether layer was separated and concentrated to provide a tan solid. This material was purified by flash chromatography using two columns (The first was eluted with 8:2 ethyl acetate:dichloromethane; the second with 1:1 ethyl acetate:dichloromethane.) to provide 0.1 g of 2-propyloxazolo[4,5-c]quinolin-4-amine as a yellow powder, m.p. 159.0–160.0° C. Analysis: Calculated for $C_{13}H_{13}N_3O$: % C, 68.71; % H, 5.77; % N, 18.49; Found: % C, 68.03; % H, 5.77; % N, 18.14.

Example 44

8-Bromo-2-propylthiazolo[4,5-c]quinolin-4-amine

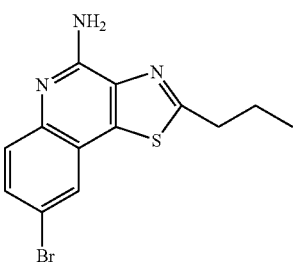

2-Propylthiazolo[4,5-c]quinolin-4-amine (1.0 g, 0.41 mmol) was combined with acetic acid (15 mL) and heated to 60° C. Bromine (0.10 mL, 1.94 mmol) was added dropwise and the reaction mixture was stirred at 60° C. for 18 hours. The reaction mixture was diluted with water and the resulting precipitate was isolated by filtration to provide 0.25 g of 8-bromo-2-propylthiazolo[4,5-c]quinolin-4-amine as a yellow solid, m.p. 177–180° C. Analysis: Calculated for $C_{13}H_{12}BrN_3S$: % C, 48.46; % H, 3.75; % N, 13.04; Found: % C, 47.98; % H, 3.95; % N, 12.70.

Example 45

7-Methyl-2-propylthiazolo[4,5-c]quinolin-4-amine

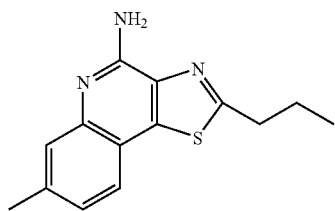

Part A

Diethyl ethoxymethylmalonate (37.8 mL, 187 mmol) and m-toluidine (20.0 mL, 187 mmol) were combined and heated at 100° C. for about 3 hours. The reaction mixture was allowed to cool to ambient temperature and it solidified. Dowtherm A (350 mL) was added and the reaction mixture was heated at reflux for about 30 minutes. The reaction mixture was allowed to cool to ambient temperature. The resulting precipitate was isolated by filtration, rinsed with acetone and dried to provide 33 g of ethyl 4-hydroxy-7-methyl-3-quinolinecarboxylate as a tan powder.

Part B

Ethyl 4-hydroxy-7-methyl-3-quinolinecarboxylate (32 g, 138 mmol) was suspended in sodium hydroxide (500 mL of 10% aqueous) and then heated at reflux for about 30 minutes. The reaction mixture was allowed to cool to ambient temperature and then it was acidified with concentrated hydrochloric acid. The resulting precipitate was isolated by filtration, rinsed well with water and then oven dried to provide 4-hydroxy-7-methyl-3-quinolinecarboxylic acid (28 g). A portion (2 g) was recrystallized twice from N,N-dimethylformamide to give a fluffy white solid, m.p. 264–265° C. Analysis: Calculated for $C_{11}H_9NO_3$: % C, 65.02; % H, 4.46; % N, 6.89; Found: % C, 65.22; % H, 4.42; % N, 6.88.

Part C

4-Hydroxy-7-methyl-3-quinolinecarboxylic acid (32 g) was placed in a round bottom flask and then heated in a Wood's metal bath at 310° C. for several minutes until all of the solids had melted into a light brown viscous liquid and bubbling had nearly ceased. The reaction mixture was allowed to cool to ambient temperature. The crude solid was recrystallized from ethyl acetate/ethanol to give 9.8 g of 7-methyl-4-quinolinol. During the recrystallization a portion of the solid did not dissolve, this material was isolated by filtration and then recrystallized to provide 1.1 g of 7-methyl-4-quinolinol as yellow-tan plates, m.p. 233–235° C. Analysis: Calculated for $C_{10}H_9NO$: % C, 75.45; % H, 5.70; % N, 8.80; Found: % C, 75.23; % H, 5.54; % N, 8.76.

Part D

Nitric acid (6 mL of 70%) was slowly added to a hot (125° C.) solution of 7-methyl-4-quinolinol (10.5 g) in propionic acid (125 mL). The reaction mixture was stirred for about 1.5 hours and then it was allowed to cool to ambient temperature. The resulting precipitate was isolated by filtration, rinsed well with ethanol and water and then dried to provide 6.9 g of 7-methyl-3-nitro-4-quinolinol as a pale yellow solid.

Part E

7-Methyl-3-nitro-4-quinolinol (11.8 g, 58 mmol), methanol (about 300 mL), ammonium hydroxide (50 mL), and palladium on carbon (1 g of 10%) were combined. The mixture was placed on a Parr apparatus under a 35–40 psi (2.4–2.8 Kg/cm²) hydrogen atmosphere for about 1 hour. The reaction mixture was filtered through a layer of Celite® filter agent and the filter cake was rinsed well with methanol. The filtrate was treated with charcoal and then concentrated under vacuum to provide a fluffy pale green solid. This material was triturated with acetonitrile to provide 8.5 g of 3-amino-7-methyl-4-quinolinol.

Part F

Under a nitrogen atmosphere, triethylamine (0.71 mL, 5.1 mmol) was added to a suspension of 3-amino-7-methyl-4-quinolinol (800 mg, 4.6 mmol) in dichloromethane (30 mL). Butyryl chloride (0.53 mL, 5.1 mmol) was added. The reaction mixture was stirred at ambient temperature for about 2 hours. Analysis by thin layer chromatography (silica gel eluting with 9:1 dichloromethane:methanol) showed starting material. The reaction mixture was heated to reflux and then inadvertently allowed to go dry over the course of about 30 minutes. More solvent was added and the reaction mixture was heated at reflux for an additional hour at which time thin layer chromatography showed no starting material. The resulting precipitate was isolated by filtration and then rinsed with dichloromethane and water to provide 650 mg of N-(4-hydroxy-7-methylquinolin-4-yl)butyramide as a pale pink-tan solid.

Part G

Under a nitrogen atmosphere, phosphorus pentasulfide (1.15 g, 2.6 mmol) was added to a mixture of N-(4-hydroxy-7-methylquinolin-4-yl)butyramide (630 mg, 2.6 mmol) in pyridine (20 mL). The reaction mixture was heated to reflux. The reaction mixture turned bright yellow and all of the solid went into solution. The reaction mixture was heated at reflux for about 2 hours and then allowed to cool to ambient temperature. The reaction mixture was extracted with water, aqueous sodium bicarbonate and dichloromethane. The organic layer was treated with saturated copper sulfate, dried with magnesium sulfate and then concentrated under vacuum to provide an oil. The oil was dried under high vacuum to provide 410 mg of 7-methyl-2-propylthiazolo[4,5-c]quinoline as an orange solid.

Part H

3-Chloroperoxybenzoic acid (2.4 g of 57–86%) was added to a mixture of 7-methyl-2-propylthiazolo[4,5-c]quinoline (2 g) and chloroform (100 mL). The reaction mixture was allowed to stir at ambient temperature for 2 hours. Analysis by thin layer chromatography showed no starting material but did show two products. The reaction mixture was stirred at ambient temperature for an additional hour and then it was extracted with dichloromethane and aqueous sodium bicarbonate. The organic layer was dried with magnesium sulfate and then concentrated under vacuum to provide a yellow-orange oil. The oil was dried under high vacuum to provide 2.1 g of 7-methyl-2-propylthiazolo[4,5-c]quinolin-5N-oxide as a solid.

Part I

Under a nitrogen atmosphere, trichloroacetyl isocyanate (1.4 mL, 12.1 mmol) was added to a mixture of 7-methyl-2-propylthiazolo[4,5-c]quinolin-5N-oxide (2.1 g, 8.1 mmol) and dichloromethane (100 mL). The resulting dark brown solution was allowed to stir at ambient temperature for about 2 hours. The reaction mixture was concentrated under vacuum to provide N-(7methyl-2-propylthiazolo[4,5-c]quinolin-4-yl)trichloroacetamide as an oil. The oil was combined with methanol and sodium methoxide (1.9 mL of 25% in methanol, 8.1 mmol) and then stirred at ambient temperature for 1 hour. The resulting precipitate was isolated by filtration and then recrystallized twice from isopropanol to provide 500 mg of 7-methyl-2-propylthiazolo[4,5-c]quinolin-4-amine as a yellow-tan powder, m.p. 186–187° C. Analysis: Calculated for $C_{14}H_{15}N_3S$: % C, 65.34; % H, 5.87; % N, 16.33; Found: % C, 64.95; % H, 5.77; % N, 16.08.

Example 46

2-Butyl-7-methyloxazolo[4,5-c]quinolin-4-amine

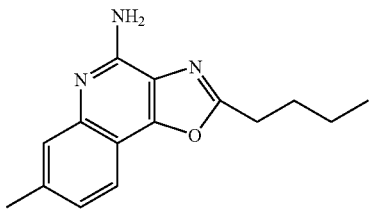

Part A

Under a nitrogen atmosphere, a mixture of 3-amino-7-methyl-4-quinolinol (5 g, 28.7 mmol) and valeric anhydride (28 mL, 143.5 mmol) was heated at reflux for about 20 hours. The reaction mixture was allowed to cool to ambient temperature, then it was made basic with 10% sodium hydroxide and stirred for an additional hour at ambient temperature. The reaction mixture was extracted with dichloromethane. The extract was dried over magnesium sulfate and then concentrated under vacuum to provide a dark brown liquid. The liquid was purified by column chromatography (silica gel eluting with 3:2 ethyl acetate:dichloromethane) to provide 4.7 g of a dark brown, semi-solid. A portion (about 700 mg) was purified by column chromatography (silica gel eluting with 95:5 dichloromethane:methanol) to provide 2-butyl-7-methyloxazolo[4,5-c]quinoline, m.p. 52–55° C. Analysis: Calculated for $C_{15}H_{16}N_2O$: % C, 74.97; % H, 6.71; % N, 11.66; Found: % C, 74.80; % H, 6.73; % N, 11.53.

Part B

3-Chloroperoxybenzoic acid (4.6 g of 57–86%) was added to a solution of 2-butyl-7-methyloxazolo[4,5-c]quinoline (3.9 g, 16.2 mmol) in chloroform (100 mL). The reaction mixture was allowed to stir at ambient temperature for 4 hours. The reaction mixture was washed with aqueous sodium bicarbonate, dried over magnesium sulfate and then concentrated under vacuum to provide 4.2 g of 2-butyl-7-methyloxazolo[4,5-c]quinolin-5N-oxide as a dark brown-orange oil.

Part C

Under a nitrogen atmosphere, trichloroacetyl isocyanate (2.9 mL, 24 mmol) was added to a mixture of 2-butyl-7-methyloxazolo[4,5-c]quinolin-5N-oxide (4.2 g, 16 mmol) and dichloromethane (100 mL). The reaction mixture was allowed to stir at ambient temperature for about 3 hours then it was concentrated under vacuum. The resulting residue was taken up in methanol and then combined with sodium methoxide (3.7 mL of 25% in methanol, 16 mmol). The reaction mixture was stirred at ambient temperature overnight. The methanol was evaporated off and the resulting residue was purified by column chromatography (silica gel eluting with 95:5 dichloromethane:methanol) to provide a brown solid. This solid was recrystallized from acetonitrile to provide 550 mg of 2-butyl-7-methyloxazolo[4,5-c]quinolin-4-amine as fine tan needles, m.p. 187–188° C. Analysis: Calculated for $C_{15}H_{17}N_3O+0.1H_2O$: % C, 70.07; % H, 6.74; % N, 16.34; Found: % C, 70.07; % H, 6.49; % N, 16.58.

Example 47

7-Methyl-2-propyloxazolo[4,5-c]quinolin-4-amine

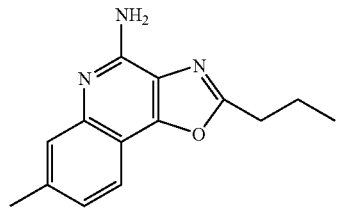

Part A

Under a nitrogen atmosphere a mixture of 3-amino-7-methyl-4-quinolinol (3.4 g, 20 mmol) and butyric anhydride (16 mL) were heated at reflux overnight. The reaction mixture was allowed to cool to ambient temperature and then it was poured over ice. The mixture was adjusted to pH 12 with 10% sodium hydroxide and then extracted with dichloromethane. The extract was dried over magnesium sulfate and then concentrated under vacuum. The residue still contained anhydride so it was combined with 10% sodium hydroxide and stirred for 1 hour at ambient temperature. The mixture was extracted with dichloromethane. The extract was dried over magnesium sulfate and then concentrated under vacuum to provide a brown oil. The oil was purified by column chromatography (silica gel eluting with 3:2 ethyl acetate:dichloromethane) to provide 3.1 g of 7-methyl-2-propyloxazolo[4,5-c]quinoline as a light brown oil which solidified on standing, m.p. 65–68° C. Analysis: Calculated for $C_{14}H_{14}N_2O$: % C, 74.31; % H, 6.24; % N, 12.38; Found: % C, 73.69; % H, 6.07; % N, 12.15.

Part B

3-Chloroperoxybenzoic acid (3.8 g of 57–86%) was added to a solution of 7-methyl-2-propyloxazolo[4,5-c]quinoline (3 g) in chloroform (100 mL). The reaction mixture was allowed to stir at ambient temperature overnight. The reaction mixture was washed twice with sodium bicarbonate, dried over magnesium sulfate and then concentrated under vacuum to provide 3.1 g of 7-methyl-2-propyloxazolo[4,5-c]quinolin-5N-oxide as a pale orange solid.

Part C

Under a nitrogen atmosphere, trichloroacetyl isocyanate (2.3 mL, 19.2 mmol) was added to a solution of 7-methyl-2-propyloxazolo[4,5-c]quinolin-5N-oxide (3.1 g, 12.8 mmol) in dichloromethane (100 mL). The reaction mixture was allowed to stir at ambient temperature for 3 hours and then the solvent was removed under vacuum. Methanol (100 mL) was added to the resulting orange residue followed by sodium methoxide (2.9 mL of 25% in methanol, 12.8 mmol). The reaction mixture was stirred at ambient temperature overnight. The resulting precipitate was isolated by filtration and then recrystallized from isopropanol to provide 450 mg of 7-methyl-2-propyloxazolo[4,5-c]quinolin-4-amine as a white solid, m.p. 188–189° C. Analysis: Calculated for $C_{14}H_{15}N_3O+0.2H_2O$: % C, 68.66; % H, 6.34; % N, 17.16; Found: % C, 68.44; % H, 6.11; % N, 17.42.

Example 48

7-Fluoro-2-propyloxazolo[4,5-c]quinolin-4-amine

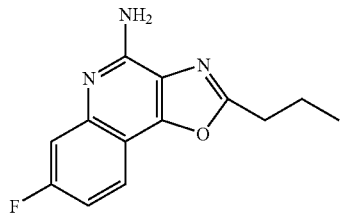

Part A

Under a nitrogen atmosphere, 3-fluoroaniline (50.0 g, 0.45 mol) and diethyl ethoxymethylmalonate (91 mL, 0.45 mol) were combined and heated at 100° C. for 3 hours. The reaction was allowed to cool to ambient temperature and it solidified. Dowtherm A (200 mL) was added and the reaction mixture was heated at 240° C. for 4 hours. The reaction mixture was allowed to cool to ambient temperature. The resulting precipitate was isolated by filtration, washed with hexane and then dried in a vacuum oven to provide 71.5 g of ethyl 7-fluoro-4-hydroxy-3-quinolinecarboxylate.

Part B

A suspension of ethyl 7-fluoro-4-hydroxy-3-quinolinecarboxylate (65 g, 0.28 mol) in 10% sodium hydroxide (250 mL) was heated at reflux for 3 hours during which time a solution was obtained. The reaction mixture was allowed to cool to ambient temperature and then it was filtered through filter paper under vacuum. The filtrate was acidified with concentrated hydrochloric acid. The resulting precipitate was collected, washed with water and then dried to provide 53.5 g of 7-fluoro-4-hydroxy-3-quinolinecarboxylic acid as a white solid.

Part C

7-Fluoro-4-hydroxy-3-quinolinecarboxylic acid (25 g) was placed in a round bottom flask and heated to 330–350° C. at which time carbon dioxide liberation commenced and the material began to liquefy. After about 2 minutes an additional 25 g of 7-fluoro-4-hydroxy-3-quinolinecarboxylic acid was added. The heating was continued for an additional 4 to 6 minutes at which time there was no further evolution of carbon dioxide. The solution was allowed to cool to ambient temperature. The resulting solid was isolated by filtration to provide 35.6 g of 7-fluoro-4-quinolinol as a pink solid.

Part D

Nitric acid (20 mL of 70%) was added to a hot (125° C.) solution of 7-fluoro-4-quinolinol (35 g, 214 mmol) in propionic acid (200 mL). The reaction mixture was stirred at 125° C. for about 1.5 hours and then allowed to cool to ambient temperature. The resulting yellow precipitate was isolated by filtration, rinsed with water and then with ethanol, and then recrystallized from N,N-dimethylformamide/water to provide 18 g of 7-fluoro-3-nitro-4-quinolinol.

Part E

A mixture containing 7-fluoro-3-nitro-4-quinolinol (17 g, 81.7 mmol), ammonium hydroxide (80 mL), methanol (200 mL) and palladium on carbon (1 g of 10% was placed on a Parr apparatus under a hydrogen atmosphere of about 30 psi (2.1 Kg/cm$^2$) for 1 hour. The reaction mixture was filtered to remove the catalyst. The filtrate was treated with charcoal then concentrated under vacuum to provide a dark tan solid which turned a very dark brown upon oven drying. The solid was dissolved in methanol then hydrochloric acid in diethyl ether was added. A gray precipitate formed almost immediately. The suspension was stirred at ambient temperature for several hours. The precipitate was isolated by filtration and rinsed well with ether to provide 6.6 g of 3-amino-7-fluoro-4-quinolinol hydrochloride.

Part F

Under a nitrogen atmosphere, 3-amino-7-fluoro-4-quinolinol hydrochloride (3.4 g, 19.1 mmol), triethylamine (2.9 mL, 21.0 mmol) and butyric anhydride (15.6 mL, 95.5 mmol) were combined and heated at reflux for about 18 hours. The reaction mixture was poured over ice and made basic to about pH 12 with 10% sodium hydroxide. The resulting suspension was stirred until all of the ice had melted then it was extracted with dichloromethane. The extract was dried over magnesium sulfate and then concentrated under vacuum to provide an oil. The oil was purified by column chromatography (silica gel eluting initially with dichloromethane and then with 9:1 dichloromethane: methanol) to provide 2.6 g of 7-fluoro-2-propyloxazolo[4,5-c]quinoline as a light brown solid.

Part G

7-Fluoro-2-propyloxazolo[4,5-c]quinoline (2.6 g, 11.3 mmol), 3-chloroperoxybenzoic acid (3.3 g of 57–86%) and chloroform (90 mL) were combined and stirred at ambient temperature for about 3 hours. Analysis by thin layer chromatography (silica gel eluting with 95:5 dichloromethane: methanol) showed starting material. An additional 0.5 equivalent of 3-chloroperoxybenzoic acid was added and the reaction was stirred at ambient temperature for another 2 hours at which time thin layer chromatography showed no starting material. The reaction mixture was diluted with dichloromethane and then washed twice with sodium bicarbonate. The organic layer was dried over magnesium sulfate and then concentrated under vacuum to provide 2.8 g of 7-fluoro-2-propyloxazolo[4,5-c]quinolin-5N-oxide as a yellow-orange oily solid.

Part H

Under a nitrogen atmosphere, trichloroacetyl isocyanate (2.0 mL, 17.0 mmol) was added to a solution of 7-fluoro-2-propyloxazolo[4,5-c]quinolin-5N-oxide (2.8 g, 11.3 mmol) in dichloromethane (50 mL). The reaction mixture was stirred at ambient temperature for 3 hours and then the dichloromethane was removed under vacuum. The residue was dissolved in methanol and then combined with sodium methoxide (2.4 mL of 25% in methanol, 11.3 mmol). The reaction mixture was stirred at ambient temperature overnight then filtered to remove a small amount of solid material. The filtrate was concentrated under vacuum. The residue was dissolved in dichloromethane, dried over magnesium sulfate and then concentrated under vacuum to provide a brown oil. The oil was purified by column chromatography (silica gel eluting with 95:5 dichloromethane:methanol) to provide a light brown sticky solid. This material was recrystallized from acetonitrile to provide 200 mg of 7-fluoro-2-propyloxazolo[4,5-c]quinolin-4- amine as a rust colored powder, m.p. 184–187° C. Analysis: Calculated for $C_{13}H_{12}FN_3O$: % C, 63.67; % H, 4.93; % N, 17.13; Found: % C, 63.43; % H, 4.57; % N, 16.74.

Example 49

7-Fluoro-2-propylthiazolo[4,5-c]quinolin-4-amine

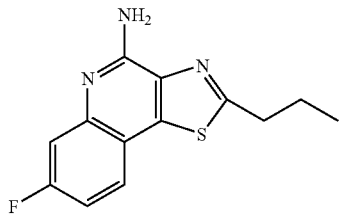

Part A

Under a nitrogen atmosphere, triethylamine (6.4 mL, 46.2 mmol) was added to a suspension of 3-amino-7-fluoro-4-quinolinol hydrochloride (3 g, 14.0 mmol) in tetrahydrofuran (50 mL). Butyryl chloride (1.6 mL, 15.4 mmol) was added dropwise at ambient temperature. The reaction mixture was stirred at ambient temperature for 4 hours. Aqueous sodium bicarbonate was added and the reaction mixture was allowed to stir at ambient temperature for about 1 hour. The resulting biphasic mixture was filtered to remove solids. The solids were rinsed with diethyl ether to provide a slightly pink powder. The tetrahydrofuran layer was concentrated under vacuum to provide a dark pink solid. This solid was triturated with ether and then oven dried. The solids were combined to provide 3.0 g of N-(7-fluoro-4-hydroxyquinolin-3-yl)butanamide. A 300 mg portion was recrystallized from ethyl acetate/ethanol to provide a light gray fluffy solid, m.p. 306–308° C. Analysis: Calculated for $C_{13}H_{13}FN_2O_2$: % C, 62.90; % H, 5.28; % N, 11.28; Found: % C, 62.95; % H, 5.34; % N, 11.14.

Part B

Under a nitrogen atmosphere, phosphorus pentasulfide (4.7 g, 10.5 mmol) was added to a mixture of N-(7-fluoro-4-hydroxyquinolin-3-yl)butanamide (2.6 g, 10.5 mmol) and pyridine (80 mL). The reaction mixture was heated at reflux for 2 hours and then allowed to cool to ambient temperature. The reaction mixture was extracted with sodium bicarbonate/dichloromethane. The organic layer was separated, washed twice with water, dried over magnesium sulfate and then concentrated under vacuum to provide a rust colored solid. This material was recrystallized from methanol to provide 1.8 g of 7-fluoro-2-propylthiazolo[4,5-c]quinoline as rust colored platelike needles.

Part C

3-Chloroperoxybenzoic acid (2.1 g of 57–86%) was added to a solution of 7-fluoro-2-propylthiazolo[4,5-c]quinoline (1.8 g, 7.3 mmol) in chloroform (50 mL). The reaction mixture was stirred at ambient temperature. Analysis by thin layer chromatography (silica gel eluting with 95:5 dichloromethane:methanol) showed starting material so an additional 0.5 equivalent of 3-chloroperoxybenzoic acid was added. The reaction mixture was stirred at ambient temperature overnight. The reaction mixture was washed twice with sodium bicarbonate, dried over magnesium sulfate and then concentrated under vacuum to provide 1.8 g of 7-fluoro-2-propylthiazolo[4,5-c]quinolin-5N-oxide as a pale orange solid.

Part D

Under a nitrogen atmosphere, trichloroacetyl isocyanate (1.2 mL, 10.4 mmol) was added to a mixture of 7-fluoro-2-propylthiazolo[4,5-c]quinolin-5N-oxide (1.8 g, 6.9 mmol) and dichloromethane (50 mL). The reaction mixture was stirred at ambient temperature for 2 hours and then concentrated under vacuum to provide N-(7-fluoro-2-propylthiazolo[4,5-c]quinolin-4-yl)trichloroacetamide as an orange oil. The oil was dissolved in methanol and then combined with sodium methoxide (1.5 mL of 25 wt % in methanol). The reaction mixture was allowed to stir at ambient temperature for 3 hours. The resulting precipitate was isolated by filtration and then recrystallized first from acetonitrile and then from methanol to provide 1.1 g of 7-fluoro-2-propylthiazolo[4,5-c]quinolin-4-amine as a tan powder, m.p. 192.5–193.5° C. Analysis: Calculated for $C_{13}H_{12}FN_3S$: % C, 59.75; % H, 4.63; % N, 16.08; Found: % C, 59.55; % H, 4.69; % N, 16.12.

Example 50

2-Propyl-7-(trifluoromethyl)thiazolo[4,5-c]quinolin-4-amine

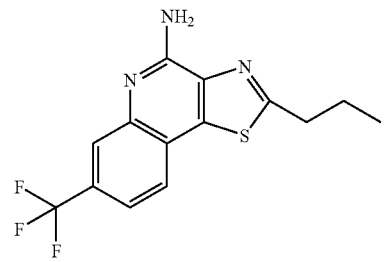

Part A

Under a nitrogen atmosphere, a mixture of 3-(trifluoromethyl)aniline (40 mL, 0.32 mmol) and diethyl ethoxymethylmalonate was heated at 100° C. for 3 hours. The reaction mixture was allowed to cool to room temperature at which time the solution solidified to provide 102 g of diethyl 2-{[3-(trifluoromethyl)anilino]methylene}malonate as a cream colored solid.

Part B

Under a nitrogen atmosphere, a mixture of 2-{[3-(trifluoromethyl)anilino]methylene}malonate (80 g, 0.24 mol) and Dowtherm A was heated to 240° C. and then stirred for 3 hours. The reaction mixture was allowed to cool to ambient temperature and then stirred for 16 hours. The solids were isolated by filtration then washed with hexane to provide 47.5 g of ethyl 4-hydroxy-7-(trifluoromethyl)-3-quinolinecarboxylate as an off-white solid.

Part C

A mixture of ethyl 4-hydroxy-7-(trifluoromethyl)-3-quinolinecarboxylate (43.4 g, 0.521 mol) and 10% sodium hydroxide (150 mL) was heated to reflux. Most of the ester did not dissolve so methanol (150 mL) was added over the course of an hour to facilitate dissolution. After refluxing for 2 hours a solution was obtained. The solution was refluxed for an additional 2 hours and then allowed to cool to ambient temperature overnight. The methanol was removed under reduced pressure and the resulting aqueous solution was acidified with concentrated hydrochloric acid. The resulting precipitate was isolated by filtration, washed with water and then dried in a vacuum oven at 120° C. for 24 hours to provide 38.5 g of 4-hydroxy-7-(trifluoromethyl)-3-quinolinecarboxylic acid as a white solid.

Part D

A round bottom flask was charged with 4-hydroxy-7-(trifluoromethyl)-3-quinolinecarboxylic acid (34.1 g, 0.132 mol) and then heated in a Wood's metal bath for 5 minutes during which time carbon dioxide evolution was observed and the material changed from a solid to a liquid. After 5 minutes no further gas evolution was noted so the flask was removed from the bath and allowed to cool to ambient temperature. The resulting solid was isolated by filtration to provide 27.75 g of 7-(trifluoromethyl)-4-quinolinol.

Part E

A mixture of 7-(trifluoromethyl)-4-quinolinol (22.7 g, 0.106 mol) and propionic acid (106 mL) was heated to 120° C. Nitric acid (10 mL of 70%) was added dropwise and heating was continued for an additional 2 hours. The reaction mixture was allowed to cool to ambient temperature. The resulting precipitate was isolated by filtration then washed with water and diethyl ether to provide 13.3 g of 3-nitro-7-(trifluoromethyl)-4-quinolinol as an off-white solid.

Part F

A Parr flask was charged with methanol (40 mL), ammonium hydroxide (10 mL), 3-nitro-7-(trifluoromethyl)-4-quinolinol (12.8 g, 49.6 mmol) and palladium on carbon (1.0 g of 10%). The mixture was placed on a Parr apparatus under a hydrogen atmosphere at 40 psi (2.8 Kg/cm$^2$) for 4 hours. The mixture was filtered and the catalyst was washed with methanol and dichloromethane. The combined organics were concentrated under vacuum to provide a green solid. The solid was dissolved in methanol and then combined with 1 N hydrochloric acid in anhydrous diethyl ether (150 mL). A precipitate formed almost immediately. The reaction mixture was allowed to stir for 16 hours. The precipitate was isolated by filtration, washed with diethyl ether and then dried in a vacuum oven at 80° C. to provide 9.3 g of 3-amino-7-(trifluoromethyl)-4-quinolinol hydrochloride as an off-white solid.

Part G

Butyryl chloride (1.5 mL, 14.5 mmol) was added dropwise to a mixture of 3-amino-7-(trifluoromethyl)-4-quinolinol hydrochloride (3.5 g, 13.2 mmol), triethylamine (6.1 mL, 43.6 mmol) and anhydrous tetrahydrofuran (30 mL). The reaction mixture was allowed to stir for 16 hours. A small amount of aqueous sodium bicarbonate was added and the reaction mixture was stirred for 0.5 hours. The tetrahydrofuran was removed under vacuum. The resulting solid was stirred with diethyl ether, isolated by filtration, washed with water and diethyl ether, and then dried in a vacuum oven at 80° C. overnight to provide 3.3 g of N-[4-hydroxy-7-(trifluoromethyl)quinolin-3-yl]butanamide as a cream colored solid.

Part H

A mixture of N-[4-hydroxy-7-(trifluoromethyl)quinolin-3-yl]butanamide (3.0 g, 10.05 mmol), phosphorous pentasulfide (4.5 g, 10.05 mmol) and pyridine (30 mL) was heated at reflux for 6 hours. The solution was allowed to cool to ambient temperature and then it was diluted with dichloromethane and aqueous sodium bicarbonate. The organic layer was separated, washed with water and with brine, dried over magnesium sulfate and then concentrated under vacuum to provide a yellow solid. This material was triturated with hexane and then isolated by filtration to provide 1.7 g 2-propyl-7-(trifluoromethyl)thiazolo[4,5-c]quinoline as a tan solid. The hexane filtrate was concentrated to give 0.6 g of additional product as a yellow solid.

Part I

3-Chloroperoxybenzoic acid (1.93 g, 6.88 mol) was added to a mixture of 2-propyl-7-(trifluoromethyl)thiazolo[4,5-c] quinoline (2.0 g, 6.75 mmol) in chloroform (30 mL). The resulting solution was allowed to stir for 24 hours. The reaction mixture was diluted with aqueous sodium bicarbonate and then extracted with dichloromethane. The organic layer was separated, dried over magnesium sulfate and then concentrated under vacuum to provide 1.98 g of 2-propyl-7-(trifluoromethyl)thiazolo[4,5-c]quinolin-5N-oxide as a yellow solid.

Part J

Under a nitrogen atmosphere, trichloroacetyl isocyanate (0.75 mL, 6.24 mmol) was added to a mixture of 2-propyl-7-(trifluoromethyl)thiazolo[4,5-c]quinolin-5N-oxide (1.3 g, 4.16 mmol) and anhydrous dichloromethane (20 mL). The resulting solution was allowed to stir at ambient temperature for 16 hours. The solvent was removed under reduced pressure. The resulting residue was dissolved in methanol (40 mL) then combined with sodium methoxide (1.43 mL of 25% in methanol, 6.24 mmol). The resulting solution was allowed to stir at ambient temperature for 16 hours by which time a precipitate had formed. The precipitate was isolated by filtration, washed with a small amount of methanol and then dried for 16 hours in a vacuum oven at 80° C. to provide 0.96 g of 2-propyl-7-(trifluoromethyl)thiazolo[4,5-c]quinolin-4-amine as a white solid, m.p. 215–16° C. Analysis: Calculated for $C_{14}H_{12}F_3N_3S$: % C, 54.01; % H, 3.89; % N, 13.50; Found: % C, 53.82; % H, 3.66; % N, 13.37.

Example 51

2-(Methylsulfonyl)thiazolo[4,5-c]quinolin-5N-oxide

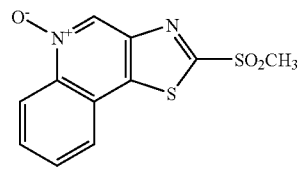

Part A

N$^4$-(2-methylpropyl)quinoline-3,4-diamine (5.4 g, 25 mmol) was combined with carbon disulfide (9 mL, 150 mmol) and ethanol (55 mL) and then heated at reflux on a steam bath for 2 hours. The resulting precipitate was isolated by filtration, washed with ethanol and then air dried to provide 4.4 g of crude product. A portion (1 g) was dissolved in hot dilute sodium hydroxide and then reprecipitated with acetic acid. The precipitate was isolated by filtration while still hot, washed with hexane and then air dried to provide thiazolo[4,5-c]quinoline-2-thiol as a solid, m.p. 282–284° C. Analysis: Calculated for $C_{10}H_6N_2S_2$: % C, 55.02; % H, 2.77; % N, 12.83: Found: % C, 54.96; % H, 2.69; % N, 12.74.

Part B

Sodium methoxide (15.8 mL of 25% in methanol, 69 mmol) and methyl iodide (3.9 mL, 63 mmol) were added to a solution of thiazolo[4,5-c]quinoline-2-thiol (13.65 g, 63 mmol) in methanol (160 mL). The reaction mixture was heated on a steam bath for 1 hour. The solvent was removed under vacuum. The resulting light green-yellow solid was slurried with water, isolated by filtration, and washed with water to provide 9.8 g of crude product. A portion (1 g) was recrystallized from methanol to provide 2-(methylthio)thiazolo[4,5-c]quinoline as a solid, m.p. 116–119° C. Analysis: Calculated for $C_{11}H_8N_2S_2$: % C, 56.87; % H, 3.47; % N, 12.06; Found: % C, 57.09; % H, 3.57; % N, 12.04.

Part C

Peracetic acid (27.8 mL of 32%, 132 mmol) was added to a mixture of 2-(methylthio)thiazolo[4,5-c]quinoline (7.7 g, 33 mmol) and acetic acid (100 mL). The reaction mixture was heated at about 60° C. for about 4 hours and then at ambient temperature overnight. The resulting yellow precipitate was isolated by filtration to give 5.6 g of crude product. The filtrate was concentrated under vacuum then the residue was diluted with toluene (100 mL). The toluene was removed under vacuum to provide an additional 4 g of crude product. A portion (1 g) was recrystallized from N,N-dimethylformamide to provide 2-(methylsulfonyl)thiazolo[4,5-c]quinolin-5N-oxide as a yellow solid, m.p. 245–247° C. Analysis: Calculated for $C_{11}H_8N_2O_3S_2$: % C, 47.13; % H, 2.88; % N, 9.99; Found: % C, 47.08; % H, 3.08; % N, 10.14.

Example 52

2-(4-Morpholino)thiazolo[4,5-c]quinoline-5N-oxide

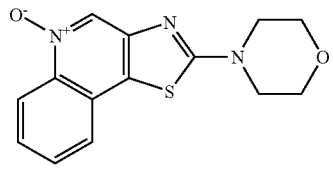

2-(Methylsulfonyl)thiazolo[4,5-c]quinolin-5N-oxide (2.5 g, 8.9 mmol) and morpholine (~50 mL) were combined and then heated on a steam bath for 9 hours. The resulting precipitate was isolated by filtration to provide 0.9 g of crude product as a yellow solid. The filtrate was cooled in an ice bath. The resulting precipitate was isolated by filtration to give 0.8 g of crude product as a yellow solid. The two crops were combined and then a portion (0.5 g) was recrystallized from methanol to provide 2-(4-morpholino)thiazolo[4,5-c]quinoline-5N-oxide as a solid, m.p. 241–242° C. Calculated for $C_{14}H_{13}N_3O_2S$: % C, 58.52; % H, 4.56; % N, 14.62; Found: % C, 58.24; % H, 4.38; % N, 14.43.

Example 53

2-(4-Morpholino)thiazolo[4,5-c]quinolin-4-amine

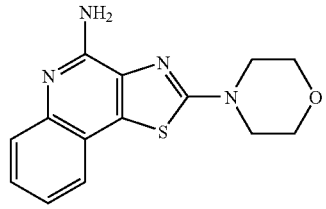

Ammonium hydroxide (18 mL) was added to a mixture of 2-(4-morpholino)thiazolo[4,5-c]quinoline-5N-oxide (1.2 g, 4.2 mmol) and dichloromethane (24 mL). The mixture was cooled and then tosyl chloride (0.88 g, 4.6 mmol) in dichloromethane (10 mL) was slowly added. The reaction mixture was warmed to ambient temperature and then stirred overnight. The organic phase was separated, washed with aqueous sodium bicarbonate, dried over magnesium sulfate and then concentrated under vacuum to provide crude product as a yellow solid. This material was purified by column chromatography then dissolved in hydrochloric acid and reprecipitated with sodium hydroxide. The precipitate was isolated by filtration and then recrystallized twice from methanol to provide 0.26 g of 2-(4-morpholino)thiazolo[4,5-c]quinolin-4-amine as a solid, m.p. 225–227° C. Analysis: Calculated for $C_{14}H_{14}N_4OS$: % C, 58.72; % H, 4.93; % N, 19.57; Found: % C, 58.47; % H, 4.63; % N, 19.23.

Example 54

2-(1-Pyrrolidino)thiazolo[4,5-c]quinolin-4-amine

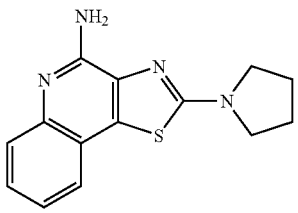

Part A 2-(Methylsulfonyl)thiazolo[4,5-c]quinolin-5N-oxide (2.5 g, 8.9 mmol) and pyrrolidine (~70 mL) were combined and then refluxed on a steam bath for 3 days. The resulting yellow precipitate was isolated by filtration to provide 0.4 g of 2-(1-pyrrolidino)thiazolo[4,5-c]quinoline-5N-oxide. The filtrate was cooled in an ice bath. The resulting precipitate was isolated by filtration to provide 0.7 g of 2-(1-pyrrolidino)thiazolo[4,5-c]quinoline-5N-oxide as a yellow solid. The two crops were combined.

Part B

Ammonium hydroxide (12 mL) was added to a mixture of 2-(1-pyrrolidino)thiazolo[4,5-c]quinoline-5N-oxide (0.8 g, 2.95 mmol) and dichloromethane (50 mL). The mixture was cooled and then tosyl chloride (0.6 g, 3.2 mmol) in dichloromethane (10 mL) was slowly added. The reaction mixture was warmed to ambient temperature and then stirred overnight. The organic phase was separated, washed with saturated aqueous sodium bicarbonate and then concentrated under vacuum to provide crude product as a yellow solid. This material was purified by flash column chromatography then slurried with hot methanol, cooled and isolated by filtration to provide 0.14 g of 2-(1-pyrrolidino)thiazolo[4,5-c]quinolin-4-amine as a solid, m.p. 259–261° C. Analysis: Calculated for $C_{14}H_{14}N_4S$: % C, 62.20; % H, 5.22; % N, 20.49; Found: % C, 61.76; % H, 5.25; % N, 20.72.

Example 55

2-Propylthiazolo[4,5-c]quinolin-4-amine Xinofoate

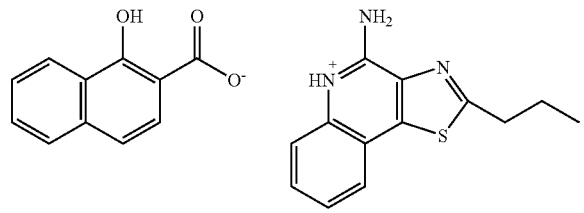

2-Propylthiazolo[4,5-c]quinolin-4-amine (3.0 g, 12.3 mmol) and 1-hydroxy-2-napthoic acid (2.3 g, 12.3 mmol) were separately dissolved in methanol with the use of dichloromethane if necessary. The two solutions were combined and the resulting solution was reduced in volume. The resulting precipitate was isolated by filtration to provide 3.6 g of 2-propylthiazolo[4,5-c]quinolin-4-amine xinofoate as a colorless crystalline solid, m.p. 185–189° C. (decomposed). Analysis: Calculated for $C_{24}H_{21}N_3O_3S$: % C, 66.80; % H, 4.91; % N, 9.74; Found: % C, 66.71; % H, 5.07; % N, 9.78.

Example 56

2-Propylthiazolo[4,5-c]quinolin-4-amine 3-Hydroxy-2-naphthoate

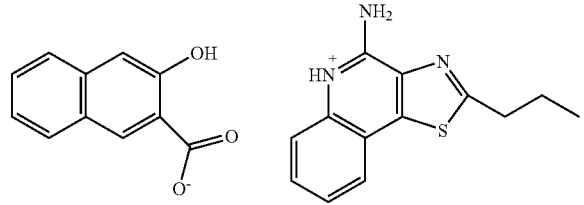

A solution of 3-hydroxy-2-naphthoic acid (1.9 g, 10 mmol) in methanol (30 mL) was added to a solution of 2-propylthiazolo[4,5-c]quinolin-4-amine (2.4 g, 10 mmol) in hot methanol (70 mL). A precipitate formed immediately. The mixture was heated an additional 5 minutes and then allowed to cool to ambient temperature. The precipitate was isolated by filtration, washed with methanol and dried to provide 4.0 g of product as a tan powder. This material was recrystallized from methanol/dichloromethane to provide 3.2 g of 2-propylthiazolo[4,5-c]quinolin-4-amine 3-hydroxy-2-naphthoate as a white powder. Calculated for $C_{24}H_{21}N_3O_3S$: % C, 66.80; % H, 4.91; % N, 9.74; Found: % C, 66.28; % H, 4.92; % N, 9.59.

Example 57

2-Butylthiazolo[4,5-c][1,5]naphthyridine-5N-oxide

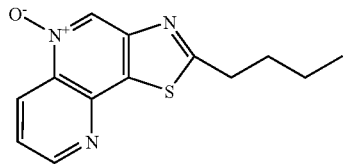

Part A

A mixture containing 3-nitro[1,5]naphthyridin-4-ol (7.5 g), methanol (200 mL), ammonium hydroxide (50 mL) and 5% platinum on carbon (0.75 g) was placed on a Parr apparatus for 6 hours. The reaction mixture was filtered to remove catalyst and then filtered a second time using Celite® filter aid. The filtrate was concentrated under vacuum to provide 6.1 g of 3-amino[1,5]naphthyridin-4-ol as a brown solid.

Part B

Valeryl chloride (4.3 g, 35 mmol) was added dropwise to a suspension of 3-amino[1,5]naphthyridin-4-ol (5.2 g, 32 mmol) in pyridine (100 mL). The reaction mixture was heated at reflux for 2 hours. The pyridine was removed. The resulting residue was taken up in hot water and then allowed to cool. The resulting gray precipitate was isolated by filtration, washed well with hot water and then oven dried to provide 2.3 g of N-(4-hydroxy[1,5]naphthyridin-3-yl)pentamide as a gray solid.

Part C

Phosphorous pentasulfide (4.2 g, 9.4 mmol) was added to a suspension of N-(4-hydroxy[1,5]naphthyridin-3-yl)pentamide (2.3 g, 9.4 mmol) in pyridine (150 mL). The reaction mixture was heated at reflux for 2 hours. The pyridine was removed. The resulting residue was taken up in a mixture of water, 10% sodium carbonate and 10% sodium hydroxide (an amount sufficient to adjust the pH to >8) and then extracted twice with dichloromethane. The dichloromethane extracts were combined, washed with brine, dried and then concentrated under vacuum. The residue was diluted with toluene and then concentrated under vacuum to provide 2 g of a black syrup. This material was purified using silica gel column chromatography to provide 1.4 g of 2-butylthiazolo[4,5-c][1,5]naphthyridine as an amber liquid. High resolution mass spec (EI): Calculated for $C_{13}H_{13}N_3S$ (M+) 243.0830; Found 243.0825

Part D

A solution of 3-chloroperoxybenzoic acid (1.1 g of 57–86%) in chloroform (50 mL) was added in a steady stream to a solution of 2-butylthiazolo[4,5-c][1,5]naphthyridine (1.4 g, 5.8 mmol) in chloroform (100 mL). The reaction mixture was stirred at ambient temperature for 2.5 hours and then it was diluted with dichloromethane, washed twice with 10% sodium hydroxide, washed with brine, dried and concentrated under vacuum to provide a light yellow syrup which solidified on standing. This material was purified by silica gel column chromatography to provide 1.2 g of a pale yellow solid. This material was recrystallized from petroleum ether (15 mL) and hexanes (100 mL) to provide 2-butylthiazolo[4,5-c][1,5]naphthyridine-5N-oxide, m.p. 65–69° C. Analysis: Calculated for $C_{13}H_{13}N_3OS$: % C, 60.21; % H, 5.05; % N, 16.20; Found: % C, 60.43; % H, 5.17; % N, 16.18. High resolution mass spec (EI): Calculated for $C_{13}H_{13}N_3OS$(M+) 259.0779; Found 259.0789.

Example 58

2-Butylthiazolo[4,5-c][1,5]naphthyridin-4-amine

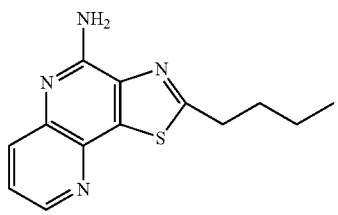

A solution of 2-butylthiazolo[4,5-c][1,5]naphthyridine-5N-oxide (0.5 g, 1.9 mmol) in dichloromethane (100 mL) was cooled in an ice bath. A solution of trichloroacetyl isocyanate (0.4 g, 2.1 mmol) in dichloromethane (25 mL) was added dropwise. The reaction mixture was stirred at ambient temperature for 8 hours. Added an amount of ammonia in methanol sufficient to make the reaction mixture basic and then let stand overnight. The reaction mixture was diluted with additional dichloromethane and then washed twice with 10% sodium hydroxide, washed with brine, dried and concentrated under vacuum to provide 0.6 g of a pale yellow solid. This material was purified by silica gel column chromatography and then recrystallized from acetonitrile (8 mL) to provide 0.15 g of 2-butylthiazolo[4,5-c][1,5]naphthyridin-4-amine as a white crystalline solid, m.p. 136–138° C. Analysis: Calculated for $C_{13}H_{14}N_4S$: % C, 60.44; % H, 5.46; % N, 21.69; Found: % C, 60.12; % H, 5.42; % N, 21.51. High resolution mass spec (EI) Calculated for $C_{13}H_{14}N_4S$ (M+) 258.0941 Found: 258.0939. NMR chemical shifts in CDCl3 (ppm) 8.637 dd (1H, J=3.6; 1.2 Hz), 8.048 dd (1H, J=8.5; 1.2 Hz), 7.486 dd (1H, J=8.5; 3.6 Hz), 5.691 bs(2H), 3.196 t (2H, J=7 Hz), 1.918 quintet (2H, J=7 Hz), 1.509 sextet (2H, J=7 Hz), 1.003 t (3H, J=7 Hz).

Example 59

2-Propylthiazolo[4,5-c][1,5]naphthyridine-5N-oxide

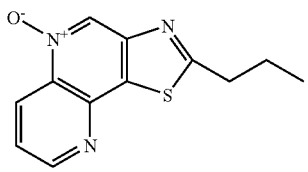

Part A

Using the general method of Example 57 Part B, 3-amino[1,5]naphthyridin-4-ol (1.8 g, 11.2 mmol) was reacted with butyryl chloride (1.3 g, 12.3 mmol) to provide 1.2 g of N-(4-hydroxy[1,5]naphthyridin-3-yl)butanamide as a charcoal gray solid, m.p. >360° C.

Part B

Using the general method of Example 57 Part C, N-(4-hydroxy[1,5]naphthyridin-3-yl)butanamide (1.2 g, 5.2 mmol) was reacted with phosphorous pentasulfide (2.3 g, 5.2 mmol) to provide 0.9 g of 2-propylthiazolo[4,5-c][1,5]naphthyridine as an amber syrup.

Part C

Using the general method of Example 57 Part D, 2-propylthiazolo[4,5-c][1,5]naphthyridine (0.9 g, 3.9 mmol) was oxidized to provide 0.7 g of 2-propylthiazolo[4,5-c][1,5]naphthyridin-5N-oxide as a pale yellow solid, m.p. 139–142° C. Analysis: Calculated for $C_{12}H_{11}N_3OS$: % C, 58.76; % H, 4.52; % N, 17.13; Found: % C, 58.66; % H, 4.59; % N, 17.16. High resolution mass spec: (EI) calculated for $C_{12}H_{11}N_3OS$ (M+) 245.0623; Found 245.0612.

Example 60

2-Propylthiazolo[4,5-c][1,5]naphthyridin-4-amine

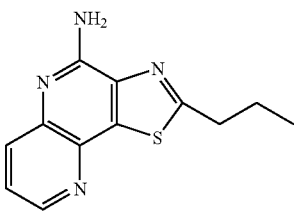

Using the general method of Example 58, 2-propylthiazolo[4,5-c][1,5]naphthyridin-5N-oxide (0.5 g, 2 mmol) was aminated to provide 0.2 g of 2-propylthiazolo[4,5-c][1,5]naphthyridin-4-amine as ivory needles, m.p. 135–136° C. Analysis: Calculated for $C_{12}H_{12}N_4S$: % C, 58.99; % H, 4.95; % N, 22.93; Found: % C, 59.06; % H, 4.96; % N, 22.97. High resolution mass spec (EI) Calculated for $C_{12}H_{12}N_4S$ (M+) 244.0783; Found 244.0785.

Example 61

2-Propylpyrido[3,4-d][1,3]thiazole-5N-oxide

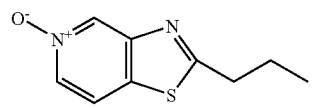

Part A

A suspension of 3-nitropyridin-4-ol (1.0 g, 7.1 mmol) in methanol (110 mL) and a small amount of raney nickel catalyst were combined in a Parr bottle and hydrogenated for 4 hours. The reaction mixture was acidified with a solution of hydrochloric acid in ethanol and then filtered to remove catalyst. The filtrate was refiltered using Celite filter aid. The filtrate was concentrated under vacuum to provide 1.2 g of 3-aminopyridin-4-ol as a brown powder, m.p. 199–200° C.

Part B

N,N-diisopropylethylamine (33 mL, 180 mmol) was added to a suspension of 3-aminopyridin-4-ol (8.5 g, 46 mmol) in dichloromethane (100 mL). A solution of butyryl chloride (5.4 g, 51 mmol) in dichloromethane (100 mL) was added dropwise. The reaction mixture was stirred at ambient temperature for 3 hours and then at reflux for 3 hours. The reaction mixture was filtered to remove a black precipitate.

The filtrate was concentrated under vacuum. The resulting light brown residue was triturated with hot ethyl acetate (250 mL) and then allowed to cool overnight. The mixture was filtered to remove solids (9.1 g) and the solids were washed with fresh ethyl acetate. The filtrate was concentrated under vacuum to provide 13 g of a light amber syrup. The syrup was dissolved in water and then extracted twice with ethyl acetate. The extracts were combined, washed with brine, dried and then concentrated under vacuum to provide 2.5 g of an amber syrup. This material was purified by column chromatography to provide 1.2 g of N-(4-hydroxypyrid-3-yl)butanamide as a light amber syrup which solidified on standing.

Part C

Using the general method of Example 57 Part C, N-(4-hydroxypyrid-3-yl)butanamide (1.1 g, 6.1 mmol) was reacted with phosphorous pentasulfide (2.7 g, 6.1 mmol) to provide 0.4 g of 2-propylpyrido[3,4-d][1,3]thiazole as an amber syrup, which solidified on standing, mp 44–47° C.

Part D

Using the general method of Example 57 Part D, 2-propylpyrido[3,4-d][1,3]thiazole (0.4 g, 2.2 mmol) was oxidized to provide 0.2 g of 2-propylpyrido[3,4-d][1,3]thiazol-5N-oxide as short ivory needles after recrystallization from ethyl acetate (7 mL), m.p.137–139° C. Analysis: Calculated for $C_9H_{10}N_2OS$: % C, 55.65; % H, 5.19; % N, 14.42; Found: % C, 55.47; % H, 5.25; % N, 14.34.

Example 62

2-Propylpyrido[3,4-d][1,3]thiazol-4-amine Trifluoroacetate

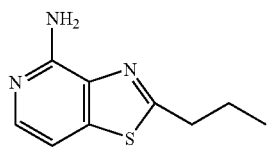

A solution of trichloroacetyl isocyanate (0.11 g, 0.6 mmol) in dichloromethane (5 mL) was added dropwise to a chilled (ice bath) solution of 2-propylpyrido[3,4-d][1,3]thiazol-5N-oxide (0.1 g, 0.5 mmol) in dichloromethane (20 mL). The reaction mixture was stirred at ambient temperature for 5 hours. Additional trichloroacetyl isocyanate (0.2 g) was added and the reaction mixture was stirred at ambient temperature overnight. The reaction mixture was briefly warmed to reflux then allowed to stir at ambient temperature for about 3 hours. Ammonia was bubbled into the reaction mixture which was then allowed to stir at ambient temperature for 1 hour. The reaction mixture was diluted with dichloromethane, washed twice with 10% sodium hydroxide, washed with brine, dried and then concentrated under vacuum to provide an amber syrup. The reaction was repeated on the same scale. The products were combined to provide 0.1 g of an amber syrup. This material was purified by semi-preparative HPLC on a Gilson system (Rainin Microsorb C18 column, 21.4×250 mm, 8 micron particle size, 60A pore, 10 mL/min., gradient elution from 2–95% B in 25 min., hold at 95% B for 5 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were lyophilized to provide the desired product as a trifluoroacetate salt m.p. 160–162° C. Analysis: Calculated for $C_9H_{11}N_3S+CF_3C(O)_2H$: % C, 42.99; % H, 3.94; % N, 13.67; Found: % C, 42.84; % H, 3.98; % N, 13.52. High resolution mass spec: (EI) calculated for $C_9H_{11}N_3S$ (M+) 193.0674; Found 193.0681.

Example 63

7-Chloro-2-propylthiazolo[4,5-c]quinolin-4-amine

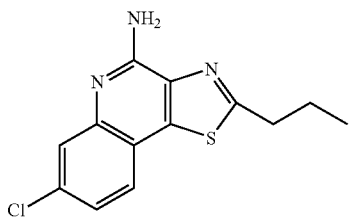

Part A

7-Chloro-4-hydroxyquinoline (35 g, 0.195 mol; available from Aldrich, Milwaukee, Wis.) and nitric acid (350 mL of 70%) were combined and heated at reflux for 75 minutes. The reaction mixture was poured over ice while still hot. The resulting bright yellow precipitate was isolated by filtration and then washed 3 times with boiling ethyl acetate to provide 17.3 g of 7-chloro-3-nitro-4-hydroxyquinoline as a pale yellow solid.

Part B

7-Chloro-3-nitro-4-hydroxyquinoline (4.48 g, 20 mmol), tin (II) chloride dihydrate (22.6 g, 100 mmol) and ethanol (200 mL) were combined and then heated at reflux for 4 hours. The reaction mixture was cooled to ambient temperature and then poured into water (250 mL). The mixture was brought to neutral pH by the addition of saturated sodium bicarbonate and then filtered to remove tin salts. The filtrate was extracted with ethyl acetate. The combined organic fractions were dried over magnesium sulfate, filtered and then concentrated under vacuum to provide 1.8 g of 3-amino-7-chloro-4-hydroxyquinoline as a green powder.

Part C

Under a nitrogen atmosphere, butyryl chloride (0.76 mL, 7.3 mmol) was added dropwise to a mixture of 3-amino-7-chloro-4-hydroxyquinoline (1.3 g, 6.7 mmol), triethylamine (3.0 mL, 21.5 mmol) and anhydrous tetrahydrofuran (20 mL). The reaction mixture was maintained at ambient temperature overnight. The resulting precipitate was isolated by filtration, washed with water followed by tetrahydrofuran, and then vacuum dried to provide 1.05 g of N-(7-chloro-4-hydroxyquinolin-3-yl)butanamide as a tan powder.

Part D

A mixture of N-(7-chloro-4-hydroxyquinolin-3-yl)butanamide (0.9 g, 3.4 mol), phosphorous pentasulfide (1.51 g, 3.4 mmol) and pyridine (25 mL) was refluxed under a nitrogen atmosphere for 2.5 hours and then allowed to cool to ambient temperature. The reaction mixture was partitioned between dichloromethane (100 mL) and sodium bicarbonate (100 mL). The aqueous layer was extracted with dichloromethane (2×100 mL). The organic fractions were combined, washed with water, dried over magnesium sulfate, filtered and then concentrated under vacuum to provide crude product. This material was purified by silica gel chromatography, (97:3 dichloromethane:methanol, 10 g SiO$_2$) to provide 0.62 g of 7-chloro-2-propylthiazolo[4,5-c]quinoline as a golden yellow solid.

Part E

Under a nitrogen atmosphere 3-chloroperoxybenzoic acid (0.7 g of 57–86%) was added to a mixture of 7-chloro-2-propylthiazolo[4,5-c]quinoline (0.5 g, 1.9 mmol) and chloroform (20 mL). After 2 hours at ambient temperature additional 3-chloroperoxybenzoic acid (0.2 g) was added and the reaction mixture was maintained at ambient temperature for 14 hours. The reaction mixture was diluted with dichloromethane and then washed twice with saturated sodium bicarbonate. The organic fraction was dried over magnesium sulfate, filtered and then concentrated under vacuum to provide 0.52 g of 7-chloro-2-propylthiazolo[4,5-c]quinoline-5N-oxide as an orange solid.

Part F

Under a nitrogen atmosphere trichloroacetyl isocyanate (0.32 mL, 2.7 mmol) was added to a mixture of 7-chloro-2-propylthiazolo[4,5-c]quinoline-5N-oxide (0.50 g, 1.8 mmol) and dichloromethane (20 mL). The reaction mixture was maintained at ambient temperature for 2 hours and then concentrated under vacuum. The resulting oily residue was dissolved in methanol (10 mL), sodium methoxide (1 mL of 25%, 4.4 mmol) was added and the reaction mixture was maintained at ambient temperature for 2.5 days. The resulting precipitate was isolated by filtration and washed with hexane to provide 0.28 g of the desired product as a golden yellow powder. A 50 mg portion was recrystallized from methanol to provide 7-chloro-2-propylthiazolo[4,5-c]quinolin-4-amine as a golden yellow crystalline solid, m.p. 159–160° C. $^1$H NMR (300 MHz, DMSO-d6) δ 7.82 (d, J=8.5 Hz, 1H), 7.60 (d, J=2.0 Hz, 1H), 7.27 (dd, J=8.5, 2.1 Hz, 1H), 7.10 (s, 2H), 3.16 (t, J=7.4 Hz, 2H), 1.87 (sextet, J=7.4 Hz, 2H), 1.02 (t, J=7.4 Hz, 3H); MS (EI) m/e 277.0441 (277.0440 calcd for C$_{13}$H$_{12}$ClN$_3$S).

Example 64

7-Methoxy-2-propylthiazolo[4,5-c]quinolin-4-amine

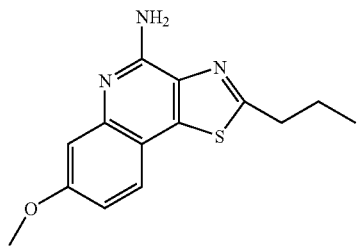

Part A

3-Methoxyaniline (12.3 g, 0.1 mol) and diethyl ethoxymethylenemalonate (21.6 g, 0.1 mol) were combined and heated at 120° C. for 3 hours. The reaction mixture was allowed to cool to ambient temperature and then placed under vacuum overnight to provide 28.5 g of diethyl 2-[3-(methoxyanilino)methylene]malonate as an orange oil.

Part B

Dowtherm A (~200 mL) was charged into a flask equipped with a stir bar, nitrogen inlet, Dean-Stark trap and condenser. The solvent was heated to a vigorous reflux and then 2-[3-(methoxyanilino)methylene]malonate (20.0 g, 68 mmol) was added. The reaction mixture was heated for 0.5 hr. and the brown solution was allowed to cool to ambient temperature. The resulting precipitate was isolated by filtration, washed with acetone and then air dried to provide 12.5 g of ethyl 4-hydroxy-7-methoxyquinoline-3-carboxylate as a yellow powder.

Part C

A suspension of ethyl 4-hydroxy-7-methoxyquinoline-3-carboxylate (12.0 g, 48 mmol) in 10% sodium hydroxide/water (200 mL) was heated at reflux for 1.5 hr. The reaction mixture was allowed to cool to ambient temperature and then made acidic (pH=3) by the dropwise addition of concentrated hydrochloric acid. The resulting precipitate was isolated by filtration, washed twice with water and then dried overnight in a vacuum oven at 80° C. to provide 10.4 g of 4-hydroxy-7-methoxyquinoline-3-carboxylic acid.

Part D

A suspension of 4-hydroxy-7-methoxyquinoline-3-carboxylic acid (4.0 g) in Dowtherm A (75 mL) was heated at reflux for 2 hrs. The resulting brown solution was allowed to slowly cool to ambient temperature. The resulting precipitate was isolated by filtration and then dried in a vacuum oven at 80° C. for 2.5 days to provide 3.1 g of 7-methoxyquinolin-4-ol as a light tan solid.

Part E

A mixture of 7-methoxyquinolin-4-ol (5.0 g, 28.5 mmol) and propionic acid (50 mL) was heated to reflux. Nitric acid (3.2 mL of 70%, 50 mmol) was added dropwise over a period of 15 minutes. The reaction mixture was refluxed for 2 hrs and then allowed to cool to ambient temperature. The resulting precipitate was isolated by filtration, washed with cold ethanol followed by hexanes and then dried to provide 3.9 g of 7-methoxy-3-nitroquinolin-4-ol as a gray solid.

Part F

7-Methoxy-3-nitroquinolin-4-ol (4.5 g, 20.4 mmol), methanol (250 mL), ammonium hydroxide (5 mL) and palladium on carbon (400 mg of 10%) were combined. The mixture was placed on a Parr apparatus under a hydrogen atmosphere at 40 psi (2.8 Kg/cm$^2$) for 2 hrs. The reaction mixture was filtered. The filtrate was concentrated under vacuum to provide a green solid. This material was dissolved in methanol (20 mL) and then 1N hydrochloric acid in diethyl ether (75 mL) was added. The resulting precipitate was isolated by filtration and dried to provide 2.6 g of 3-amino-7-methoxyquinolin-4-ol hydrochloride as a pink solid.

Part G

Butyryl chloride (0.63 mL, 6.1 mmol) was added dropwise to a solution containing 3-amino-7-methoxyquinolin-4-ol hydrochloride (1.0 g, 5.26 mmol), triethylamine (2.35 mL, 16.8 mmol), dichloromethane (30 mL) and N,N-dimethylformamide (10 mL). The reaction mixture was maintained at ambient temperature overnight. The N,N-dimethylformamide was removed under vacuum and the resulting solid was partitioned between dichloromethane (100 mL) and water (100 mL). The organic fraction was washed with water, dried over magnesium sulfate, filtered and then concentrated under vacuum to provide 0.86 g of N-(4-hydroxy-7-methoxyquinolin-3-yl)butanamide as a tan solid.

Part H

Under a nitrogen atmosphere a mixture of N-(4-hydroxy-7-methoxyquinolin-3-yl)butanamide (0.66 g, 2.54 mmol), pyridine (20 mL), and phosphorous pentasulfide (1.13 g, 2.54 mmol) was heated at reflux and then cooled to ambient temperature. The reaction mixture was filtered. The filtrate was partitioned between dichloromethane (100 mL) and saturated sodium bicarbonate (100 mL). The aqueous fraction was extracted with additional dichloromethane (100 mL). The organic fractions were combined, washed with water, dried over magnesium sulfate, filtered and then concentrated under vacuum to provide a solid. This material was purified by silica gel chromatography (15 g of $SiO_2$ eluting with 95:5 dichloromethane:methanol) to provide 0.45 g of 7-methoxy-2-propylthiazolo[4,5-c]quinoline as a pale yellow powder.

Part I

Using the method of Example 63 Part E, 7-methoxy-2-propylthiazolo[4,5-c]quinoline (0.40 g, 1.55 mmol) was oxidized to provide 7-methoxy-2-propylthiazolo[4,5-c]quinoline-5N-oxide as an orange solid.

Part J

Using the method of Example 63 Part F, the N-oxide from Part I was reacted with trichloroacetyl isocyanate and the resulting amide was hydrolyzed to provide 190 mg of the desired product as an off white solid. An analytical sample was obtained by recrystallization from methanol to provide 7-methoxy-2-propylthiazolo[4,5-c]quinolin-4-amine as off-white needles, m.p. 152–154° C. $^1$H NMR (300 MHz, DMSO-d6) δ 7.67 (d, J=8.7 Hz, 1H), 7.06 (d, J=2.4 Hz, 1H), 6.91 (dd, J=8.7, 2.5 Hz, 1H), 6.82 (s, 2H), 3.86 (s, 3H), 3.11 (t, J=7.4 Hz, 2H), 1.85 (sextet, J=7.4 Hz, 2H), 1.01 (t, J=7.4 Hz, 3H); MS (EI) m/e 273.0934 (273.0936 calcd for $C_{14}H_{15}N_3OS$).

Interferon (α) Induction 1N Human Cells

An in vitro human blood cell system was used to assess interferon induction by compounds of the invention. Activity is based on the measurement of interferon secreted into culture media. Interferon is measured by bioassay.

Blood Cell Preparation for Culture

Whole blood is collected by venipuncture into EDTA vacutainer tubes. Peripheral blood mononuclear cells (PBM's) are separated from whole blood by using either LeucoPREP™ Brand Cell Separation Tubes (available from Becton Dickinson) or Ficoll-Paque® solution (available from Pharmacia LKB Biotechnology Inc, Piscataway, N.J.). The PBM's are suspended at $1 \times 10^6$/mL in RPMI 1640 media (available from GIBC(O), Grand Island, N.Y.) containing 25 mM HEPES (N-2-hydroxyethylpiperazine-N'-2-ethanesulfonic acid) and L-glutamine (1% penicillin-streptomycin solution added) with 10% heat inactivated (56° C. for 30 minutes) fetal calf serum added. 200 μL portions of PBM suspension are added to 96 well (flat bottom) sterile tissue culture plates (Becton Dickinson Labware, Lincoln Park, N.J.).

Compound Preparation

The compounds are solubilized in ethanol, dimethyl sulfoxide or tissue culture water then diluted with tissue culture water, 0.01N sodium hydroxide or 0.01N hydrochloric acid (The choice of solvent will depend on the chemical characteristics of the compound being tested.). Ethanol or DMSO concentration should not exceed a final concentration of 1% for addition to the culture wells. Compounds are initially tested in a concentration range of from about 0.1 μg/mL to about 5 μg/mL. Compounds which show induction at a concentration of 0.5 μg/mL are then tested in a wider concentration range.

Incubation

The solution of test compound is added in a volume (less than or equal to 50 μL) to the wells containing 200 μL of diluted whole blood or of PBM's in media. Solvent and/or media is added to control wells (wells with no test compound) and as needed to adjust the final volume of each well to 250 μL. The plates are covered with plastic lids, vortexed gently and then incubated for 48 hours at 37° C. with a 5% carbon dioxide atmosphere.

Separation

Following incubation, the plates are covered with parafilm and then centrifuged at 1000 rpm for 10 to 15 minutes at 4° C. in a Damon IEC Model CRU-5000 centrifuge. Media (about 200 μL) is removed from 4 to 8 wells and pooled into 2 mL sterile freezing vials. Samples are maintained at −70° C. until analysis.

Interferon Analysis/Calculation

Interferon is determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates", Biotechniques, June/Jul. 78, 1983, incorporated herein by reference. Briefly stated the method is as follows: interferon dilutions and A549 cells are incubated at 37° C. for 12 to 24 hours. The incubated cells are infected with an inoculum of encephalomyocarditis virus. The infected cells are incubated for an additional period at 37° C. before quantifying for viral cytopathic effect. The viral cytopathic effect is quantified by staining followed by spectrophotometric absorbance measurements. Results are expressed as alpha reference units/mL based on the value obtained for NIH HU IF-L standard. The interferon was identified as essentially all interferon alpha by testing in checkerboard neutralization assays against rabbit anti-human interferon (beta) and goat anti-human interferon (alpha) using A549 cell monolayers challenged with encephalomyocarditis virus.

Compounds of the invention were tested for their ability to induce interferon in human cells using the test method described above. The results are given in the table below where "+" indicates that the compound induced interferon a at that particular concentration, a "−" indicates that the compound did not induce interferon α at that particular concentration, and a "±" indicates that the results were equivocal at that particular concentration.

Interferon (α) Induction in Human Cells

| Example | Dose Concentration (μg/mL) | | | | | | | | |
|---|---|---|---|---|---|---|---|---|---|
| | 0.01 | 0.05 | 0.10 | 0.50 | 1.0 | 5.0 | 10.0 | 25.0 | 50.0 |
| 2 | − | − | ± | + | + | + | not run | not run | not run |
| 4 | − | − | − | + | + | + | not run | not run | not run |
| 5 | − | − | − | − | + | + | + | + | + |
| 8 | − | − | − | + | + | + | not run | not run | not run |
| 12 | − | + | + | + | + | + | not run | not run | not run |
| 14 | − | − | − | + | + | + | not run | not run | not run |
| 16 | − | − | − | − | + | + | not run | not run | not run |
| 18 | − | − | + | + | + | + | not run | not run | not run |
| 20 | − | − | − | − | − | + | + | + | + |
| 22 | − | − | − | − | − | − | + | + | + |
| 24 | − | − | − | − | − | − | + | + | + |
| 26 | − | − | − | − | − | + | + | + | + |
| 28 | − | − | − | + | + | + | not run | not run | not run |
| 30 | − | − | − | − | + | + | not run | not run | not run |
| 32 | − | − | ± | + | + | + | not run | not run | not run |
| 34 | − | − | − | − | − | − | not run | not run | not run |
| 36 | − | − | − | − | + | + | not run | not run | not run |
| 37 | − | − | − | − | − | − | not run | not run | not run |
| 38 | − | − | − | + | + | + | not run | not run | not run |
| 39 | − | − | + | + | + | + | not run | not run | not run |
| 41 | + | + | + | + | + | + | not run | not run | not run |
| 42 | − | − | − | + | + | + | not run | not run | not run |
| 43 | − | + | + | + | + | + | not run | not run | not run |
| 44 | not run | not run | − | − | − | + | + | + | + |
| 45 | − | + | + | + | + | + | not run | not run | not run |
| 46 | − | + | + | + | + | + | not run | not run | not run |
| 47 | − | + | + | + | + | + | not run | not run | not run |
| 48 | − | − | − | + | + | + | not run | not run | not run |
| 49 | − | − | − | + | + | + | not run | not run | not run |
| 50 | not run | not run | − | + | + | + | + | + | + |
| 53 | − | − | − | − | − | − | − | + | + |
| 54 | − | − | − | − | − | − | − | + | + |

Cytokine Induction in Human Cells

An in vitro human blood cell system was used to assess cytokine induction by compounds of the invention. Activity is based on the measurement of interferon (α) and tumor necrosis factor (α) (IFN and TNF, respectively) secreted into culture media as described by Testerman et. al. In "Cytokine Induction by the Immunomodulators Imiquimod and S-27609", *Journal of Leukocyte Biology*, 58, 365–372 (September, 1995).

Blood Cell Preparation for Culture

Whole blood is collected by venipuncture into EDTA vacutainer tubes from healthy human donors. Peripheral blood mononuclear cells (PBMCs) are separated from whole blood by density gradient centrifugation using Histopaque®-1077 (Sigma Chemicals, St. Louis, Mo.). The PBMCs are suspended at 3–4×10$^6$ cells/mL in RPMI 1640 medium containing 10% fetal bovine serum, 2 mM L-glutamine and 1% penicillin/streptomycin solution (RPMI complete). The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested in a concentration range of from 0.12 to 30 μM.

Incubation

The solution of test compound is added at 60 μM to the first well containing RPMI complete and serial 3 fold dilutions are made. The PBMC suspension is then added to the wells in an equal volume, bringing the test compound concentrations to the desired range (0.12 to 30 μM). The final concentration of PBMC suspension is 1.5–2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200×g) at 4° C. The cell culture supernatant is removed with a sterile polypropylene pipet and transferred to sterile polypropylene tubes. Samples are maintained at −30 to −70° C. until analysis. The samples are analyzed for interferon (α) by either ELISA or bioassay and for tumor necrosis factor (α) by ELISA Interferon Bioassay Analysis Interferon is determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates", *Biotechniques*, June/July, 78, (1983), incorporated herein by reference. Briefly stated the method is as follows: A549 cells are incubated with dilutions of samples or a standard interferon at 37° C. for 24 hours. The incubated cells are then infected with an inoculum of encephalomyocarditis virus. The infected cells are incubated for an additional 24 hours at 37° C. before evaluating for viral cytopathic effect. The viral cytopathic effect is quantified by staining with crystal violet followed by visual scoring of the plates. Results are expressed as alpha reference units/mL based on the value obtained for NIH Human Leukocyte IFN standard.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. according to the manufacturer's instructions.

Tumor necrosis factor (α) (TNF) concentration is determined using ELISA kits available from Genzyme, Cambridge, Mass.; R&D Systems, Minneapolis, Minn.; or Pharmingen, San Diego, Calif. according to the manufacturer's instructions.

In the tables below, a "+" indicates that the compound induced the indicated cytokine at that particular concentration, a "−" indicates that the compound did not induce the indicated cytokine at that particular concentration, and a "±" indicates that the results were equivocal at that particular concentration.

| | Cytokine Induction in Human Cells | | | | | | | | | | | |
|---|---|---|---|---|---|---|---|---|---|---|---|---|
| | Interferon (α) Induction Dose Concentration (μM) | | | | | | Tumor Necrosis Factor Induction Dose Concentration (μM) | | | | | |
| Example | 0.12 | 0.37 | 1.11 | 3.33 | 10 | 30 | 0.12 | 0.37 | 1.11 | 3.33 | 10 | 30 |
| 12 | − | − | − | + | + | + | + | + | + | + | + | + |
| 18 | − | − | + | + | + | + | + | + | + | + | + | + |
| 20 | − | − | + | − | − | − | − | − | − | + | + | + |
| 24 | − | − | − | − | − | − | − | − | − | − | − | + |
| 42 | − | − | − | − | + | − | − | − | + | + | + | + |
| 53 | − | − | − | − | − | − | − | − | − | − | − | − |
| 58 | − | − | − | − | ± | ± | − | + | + | + | + | + |
| 60 | − | − | − | − | − | − | − | ± | + | + | + | + |
| 62 | − | − | − | − | − | − | − | − | − | − | − | − |
| 63 | − | − | + | + | + | − | + | + | + | + | + | + |
| 64 | − | + | + | + | + | + | + | + | + | + | + | + |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A method of inducing cytokine biosynthesis in a mammal comprising administering a composition comprising a therapeutically effective amount of a compound of the formula I:

wherein:
- $R_1$ is selected from the group consisting of oxygen and sulfur;
- $R_2$ is selected from the group consisting of alkyl and alkoxyalkyl; and
- $R_3$ and $R_4$ are taken together to form a fused pyridine ring;

a pharmaceutically acceptable salt thereof, with a pharmaceutically acceptable carrier, to the mammal; wherein the cytokine comprises IFN-α and/or TNF-α.

2. The method of claim 1 wherein the composition is administered topically.

3. The method of claim 1 wherein $R_1$ is sulfur.

UNITED STATES PATENT AND TRADEMARK OFFICE
CERTIFICATE OF CORRECTION

PATENT NO. : 7,148,232 B2
APPLICATION NO. : 10/926385
DATED : December 12, 2006
INVENTOR(S) : John F. Gerster It is certified that error appears in the above-identified patent and that said Letters Patent is hereby corrected as shown below:

Column 16:
Line 59, After "Found" insert -- : --.

Column 17:
Line 7, Delete "$C_{11}H_9N_3S$ HCl:" and insert -- $C_{11}H_9N_3S$ • HCl: --, therefor.

Column 18:
Line 6, Delete "$C_{10}H_7N_3S$ HCl $H_2O$:" and insert -- $C_{10}H_7N_3S$ • HCl • $H_2O$: --, therefor.

Column 20:
Lines 43-44, Delete "Alternative Synthesis" and insert the same on line 44 as a heading".

Column 21:
Line 42, Delete "$C_{12}H_{11}N_3S$ HCl:" and insert -- $C_{12}H_{11}N_3S$ • HCl: --, therefor.

Column 22:
Lines 37-38, Delete "Alternative Synthesis" and insert the same on line 38 as a heading".

Column 23:
Line 11, Delete "$C_{13}H_{13}N_3S$ HCl:" and insert -- $C_{13}H_{13}N_3S$ • HCl: --, therefor.

Column 28:
Line 66, Delete "$C_{14}H_{14}N_2O_2S$ $1/3H_2O$:" and insert -- $C_{14}H_{14}N_2O_2S$ • $1/3H_2O$: --, therefor.

Column 61:
Line 42, Delete "1N" and insert -- in --, therefor.

UNITED STATES PATENT AND TRADEMARK OFFICE
CERTIFICATE OF CORRECTION

PATENT NO. : 7,148,232 B2
APPLICATION NO. : 10/926385
DATED : December 12, 2006
INVENTOR(S) : John F. Gerster It is certified that error appears in the above-identified patent and that said Letters Patent is hereby corrected as shown below:

<u>Column 62:</u>
Line 63, After "interferon" delete "a" and insert -- α --, therefor.

Signed and Sealed this

Fourteenth Day of August, 2007

JON W. DUDAS
*Director of the United States Patent and Trademark Office*